(12) United States Patent
Priestley et al.

(10) Patent No.: US 7,247,654 B2
(45) Date of Patent: Jul. 24, 2007

(54) 3,4-DISUBSTITUTED BENZAMIDINES AND BENZYLAMINES, AND ANALOGUES THEREOF, USEFUL AS SERINE PROTEASE INHIBITORS

(75) Inventors: E. Scott Priestley, Yardley, PA (US); Xiaojun Zhang, Furlong, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 508 days.

(21) Appl. No.: 10/858,364

(22) Filed: Jun. 1, 2004

(65) Prior Publication Data

US 2005/0009895 A1 Jan. 13, 2005

Related U.S. Application Data

(60) Provisional application No. 60/475,645, filed on Jun. 4, 2003.

(51) Int. Cl.
*A61K 31/24* (2006.01)
*C07C 229/52* (2006.01)

(52) U.S. Cl. .................. 514/535; 514/539; 560/27; 560/43; 562/452; 562/455

(58) Field of Classification Search .............. 560/27, 560/43; 562/452, 455; 514/535, 539
See application file for complete search history.

(56) References Cited

U.S. PATENT DOCUMENTS

| 5,023,236 A | 6/1991 | Edgington et al. |
| 5,843,442 A | 12/1998 | Soule et al. |
| 5,866,542 A | 2/1999 | Vlasuk et al. |

FOREIGN PATENT DOCUMENTS

| WO | WO 02/062778 | 8/2002 |
| WO | WO 02/064578 | 8/2002 |
| WO | WO 02/064598 | 8/2002 |
| WO | WO 02/064599 | 8/2002 |
| WO | WO 2004/048335 | 6/2004 |

OTHER PUBLICATIONS

Lorrain et al., The Journal of Pharmacology and Experimental Therapeutics, vol. 304, No. 2, (2002), pp. 567-574.*
Yokota et al., Jpn. J. Pharmacol. 68, 201-206 (1995).*
Wong et al., The Journal of Pharmacology and Experimental Therapeutics, vol. 295, No. 1, (2000), pp. 212-218.*
Carson, S.D. et al., "The role of tissue factor in the production of thrombin", Blood Coagulation and Fibinolysis, vol. 4, pp. 281-292 (1993).
Colman, R.W., Chapter 6: "Contact Activation Pathway: Inflammatory, Fibrinolytic, Anticoagulant, Antiadhesive, and Antiangiogenic Activities", Hemostasis and Thrombosis: Basic Principles and Clinical Practice, Fourth Edition, Lippincott Williams & Wilkins, publ., Colman, R.W. et al., eds., pp. 103-121 (2001).
Girard, T.J. et al., "The role of tissue factor/factor VIIa in the pathophysiology of acute thrombotic formation", Current Opinion in Pharmacology, vol. 1, pp. 159-163 (2001).
Schmaier, A.H., Chapter 5: "Contact Activation", Thrombosis and Hemorrhage, Second Edition, Williams & Wilkins, publ., Loscalzo, J. et al., eds., pp. 105-127 (1998).

* cited by examiner

*Primary Examiner*—Kamal A. Saeed
*Assistant Examiner*—Rebecca Anderson
(74) *Attorney, Agent, or Firm*—Jing G. Sun

(57) ABSTRACT

The present invention relates generally to compounds that inhibit serine proteases. In particular it is directed to novel 3,4-disubstituted benzamidines and benzylamines, or a stereoisomer or pharmaceutically acceptable salt form thereof, which are useful as selective inhibitors of serine protease enzymes of the coagulation cascade; for example thrombin, factor Xa, factor XIa, factor IXa, and/or factor VIIa. In particular, it relates to compounds that are factor VIIa inhibitors. This invention also relates to pharmaceutical compositions comprising these compounds and methods of using the same.

20 Claims, No Drawings

3,4-DISUBSTITUTED BENZAMIDINES AND BENZYLAMINES, AND ANALOGUES THEREOF, USEFUL AS SERINE PROTEASE INHIBITORS

CROSS-REFERENCE TO RELATED APPLICATIONS

The present application claims the priority benefit of U.S. Provisional Application No. 60/475,645, filed Jun. 4, 2003, which is expressly incorporated fully herein by reference.

FIELD OF THE INVENTION

The present invention provides novel 3,4-disubstituted benzamidines and benzylamines, and analogues thereof, which are selective inhibitors of serine protease enzymes of the coagulation cascade and/or contact activation system; for example thrombin, factor VIIa, factor Xa, factor XIa, factor IXa, and/or plasma kallikrein. In particular, it relates to compounds that are factor VIIa inhibitors. This invention also relates to pharmaceutical compositions comprising these compounds and methods of using the same.

BACKGROUND OF THE INVENTION

Factor VIIa is a plasma serine protease involved in the initiation of the coagulation cascade. It binds with high affinity to tissue factor in the presence of calcium ions to form a complex with enhanced proteolytic activity (Carson, S. D. and Brozna, J. P. *Blood Coag. Fibrinol.* 1993, 4, 281-292). The tissue factor/factor VIIa complex initiates blood coagulation by proteolytic cleavage of factor X to factor Xa, factor IX to factor IXa and additional factor VII to VIIa. Ultimately, the activity of factor VIIa induces the conversion of prothrombin to thrombin. Thrombin converts fibrinogen to fibrin, which forms a clot through polymerization.

While blood coagulation is essential to the regulation of an organism's hemostasis, it is also involved in many pathological conditions. For instance, thrombosis, or formation of a clot which obstructs circulation, plays a key role in unstable angina, myocardial infarction, ischemic stroke, deep vein thrombosis, perpipheral occlusive arterial disease, pulmonary embolism, and other diseases.

Because of its key role in the coagulation cascade, researchers have postulated that inhibition of factor VIIa could be used to treat or prevent thrombotic disease. (Girard, T. J.; Nicholson, N. S. *Curr. Opin. Pharmacol.* 2001, 1, 159-163). Work has accordingly been performed to identify and optimize factor VIIa inhibitors. For example, U.S. Pat. No. 5,866,542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998). Because plasma kallikrein plays a key role in the contact activation process, inhibitors of plasma kallikrein are anticipated to block contact activation and be therapeutically useful for treatment of inflammatory and/or thrombotic disease.

Plasma kallikrein is a zymogen of a trypsin-like serine protease and is present in plasma at 35 to 50 µg/mL. The gene structure is similar to that of factor XI, overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Separate from the compounds reported herein, some benzamidine and benzylamine compounds have been reported in WO 02/62778 as antithrombotic compounds; and in WO 02/64578, WO 02/64598, and WO 02/64599 as matrix metalloproteinase inhibitors. The scope of the present invention is considered not to be exemplified nor suggested by the above references.

While a number of factor VIIa inhibitors have been discussed in the art, improved inhibitors, especially non-peptide inhibitors, of serine proteases for the treatment of thromboembolic disorders are always desirable. The present invention discloses 3,4-disubstituted benzamidines and benzylamines, and analogues thereof, as non-peptide inhibitors inhibitors of coagulation Factor VIIa and/or plasma kallikrein and as such are useful in the treatment of thromboembolic and/or inflammatory disorders.

In addition, it is also desirable to find new compounds with improved pharmacological characteristics compared with known serine protease inhibitors. For example, it is preferred to find new compounds with improved factor VIIa inhibitory activity and selectivity for factor VIIa versus other serine proteases. Also, it is preferred to find new compounds with improved plasma kallikrein inhibitory activity and selectivity for plasma kallikrein versus other serine proteases. It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f)

factors that decrease the potential for adverse side-effects; and, (g) factors that improve manufacturing costs or feasibility.

SUMMARY OF THE INVENTION

Accordingly, the present invention provides novel 3,4-disubstituted benzamidines and benzylamines, which are useful as selective inhibitors of serine protease enzymes, especially factor VIIa and/or plasma kallikrein, or stereoisomers or pharmaceutically acceptable salts, solvates, or prodrugs thereof.

The present invention also provides pharmaceutical compositions comprising a pharmaceutically acceptable carrier and a therapeutically effective amount of at least one of the compounds of the present invention or stereoisomers or pharmaceutically acceptable salts, solvates, or prodrugs thereof.

The present invention also provides a method for modulation of the coagulation cascade and/or the contact activation system comprising administering to a host in need of such treatment a therapeutically effective amount of at least one of the compounds of the present invention or stereoisomers or pharmaceutically acceptable salts, solvates, or prodrugs thereof.

The present invention also provides a method for treating thromboembolic disorders comprising administering to a host in need of such treatment a therapeutically effective amount of at least one of the compounds of the present invention or a stereoisomer or a pharmaceutically acceptable salt, solvate, or prodrug form thereof.

The present invention also provides a method for treating inflammatory diseases disorders comprising administering to a host in need of such treatment a therapeutically effective amount of at least one of the compounds of the present invention or a stereoisomer or a pharmaceutically acceptable salt or prodrug form thereof.

The present invention also provides novel 3,4-disubstituted benzamidines and benzylamines for use in therapy.

The present invention also provides the use of novel 3,4-disubstituted benzamidines and benzylamines for the manufacture of a medicament for the treatment of a thromboembolic disorder.

The present invention also provides the use of novel 3,4-disubstituted benzamidines and benzylamines for the manufacture of a medicament for the treatment of an inflammatory disorder.

These and other embodiments, which will become apparent during the following detailed description, have been achieved by the inventors' discovery that the presently claimed novel compounds of the present invention, or pharmaceutically acceptable salt or prodrug forms thereof, are effective factor VIIa inhibitors and/or plasma kallikrein inhibitors.

DETAILED DESCRIPTION OF PREFERRED EMBODIMENTS

In a first aspect, the present invention provides, inter alia, compounds of Formula (I):

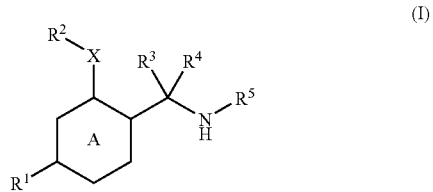

or a stereoisomer or pharmaceutically acceptable salt, solvate, or prodrug form thereof, wherein:

ring A is phenyl or a 6-membered heteroaryl consisting of carbon atoms and 1-2 N; wherein the phenyl or heteroaryl is further substituted with 0-2 $R^6$;

X is $NR^7$ or O;

$R^1$ is $-CH_2NR^{1a}R^{1b}$ or $-C(=NR^{1c})NHR^{1d}$;

$R^{1a}$ is, independently at each occurrence, H or $C_1$-$C_3$ alkyl;

$R^{1b}$ is, independently at each occurrence, H or $C_1$-$C_3$ alkyl;

$R^{1c}$ is, independently at each occurrence, H, $C_1$-$C_4$ alkyl, $-OH$, $-OR^{1e}$, $-C(O)OR^{1e}$, $-OC(O)R^{1e}$, $-OC(O)OR^{1e}$, $-OC(O)NR^{1a}R^{1e}$, $-OS(O)_2R^{1e}$, $-NH_2$, $-NR^{1a}R^{1e}$, $-NR^{1a}C(O)R^{1e}$, $-NR^{1a}C(O)OR^{1e}$, $-NR^{1a}C(O)R^{1a}R^{1e}$, $-C(O)R^{1e}$, $-CH_2OC(O)R^{1e}$, $-S(O)_2R^{1e}$, $-C(O)SR^{1e}$, $-C(S)OR^{1e}$, or $-C(S)SR^{1e}$;

$R^{1d}$ is, independently at each occurrence, H, $C_1$-$C_4$ alkyl, $-OH$, $-OR^{1e}$, $-C(O)OR^{1e}$, $-OC(O)R^{1e}$, $-OC(O)OR^{1e}$, $-OC(O)NR^{1a}R^{1e}$, $-OS(O)_2R^{1e}$, $-NH_2$, $-NR^{1a}R^{1e}$, $-NR^{1a}C(O)R^{1e}$, $-NR^{1a}C(O)OR^{1e}$, $-NR^{1a}C(O)R^{1a}R^{1e}$, $-C(O)R^{1e}$, $-CH_2OC(O)R^{1e}$, $-S(O)_2R^{1e}$, $-C(O)SR^{1e}$, $-C(S)OR^{1e}$, or $-C(S)SR^{1e}$;

alternatively, $R^{1c}$ and $R^{1d}$ are taken together to form $-C(O)OC(O)-$, $-C(O)O-$, $-C(O)S-$, $-C(S)S-$, $-C(S)O-$, $-S(O)_2O-$, $-S(O)O-$, $-OC(O)O-$, $-OC(OR^{1e})=$, $-OC(CF_3)=$, $-OC(R^{1h}R^{1i})-$, or $-OC(R^{1h}R^{1i})O-$;

$R^{1e}$ is, independently at each occurrence, $R^{1f}$, $C_1$-$C_6$ alkyl substituted with 1 $R^{1f}$, $C_1$-$C_8$ alkyl substituted with 0-3 $R^{1g}$, $C_2$-$C_6$ alkenyl substituted with 0-3 $R^{1g}$, or $C_2$-$C_6$ alkynyl substituted with 0-3 $R^{1g}$;

$R^{1f}$ is, independently at each occurrence, $C_3$-$C_{13}$ mono- or bicycloalkyl substituted with 0-3 $R^{1g}$, $C_6$-$C_{10}$ aryl substituted with 0-3 $R^{1g}$, or 5-14 membered unsaturated, partially unsaturated or saturated heterocyclyl consisting of carbon atoms and 1-4 heteroatoms independently chosen from O, N, and S, and substituted with 0-3 $R^{1g}$;

$R^{1g}$ is, independently at each occurrence, halogen, $-CF_3$, $C_1$-$C_6$ alkyl, $-OH$, $C_1$-$C_6$ alkoxy, $-CN$, $-NO_2$, $-NH_2$, $-N(CH_3)_2$, $=O$, $-COOH$, $-C(O)OC_1$-$C_6$ alkyl, or $-OC(O)$aryl;

$R^{1h}$ is, independently at each occurrence, $C_1$-$C_6$ alkyl or phenyl;

$R^{1i}$ is, independently at each occurrence, $C_1$-$C_6$ alkyl or phenyl;

alternatively, $R^{1h}$ and $R^{1i}$ are taken together to form $-CH_2CH_2-$, $-CH_2CH_2CH_2-$, $-CH_2CH_2CH_2CH_2-$, or $-CH_2CH_2CH_2CH_2CH_2-$;

$R^2$ is Y-Z-$R^{2a}$;

Y is a bond, $C_1$-$C_8$ alkylene substituted with 0-3 $R^{2d}$, $C_2$-$C_8$ alkenylene substituted with 0-3 $R^{2d}$, or $C_2$-$C_8$ alkynylene substituted with 0-3 $R^{2d}$;

Z is absent, a bond, $-O-$, $-OC(O)-$, $-OC(O)O-$, $-OC(O)NR^{2b}-$, $-NR^{2b}-$, $-NR^{2b}C(O)-$, $-NR^{2b}C(O)$ O—, —NR$^{2b}$C(O)NR$^{2b}$—, —NR$^{2b}$S(O)$_2$—, —NR$^{2b}$S(O)$_2$NR$^{2b}$—, —S(O)$_2$N$^{2b}$—, —S(O)$_2$—, —S(O)—, —C(O)O—, —C(O)NR$^{2b}$—, or —C(O)—;

provided that X—Y-Z do not combine to form a N—O, O—N, O—O, or O—S(O)$_p$ bond;

R$^{2a}$ is, independently at each occurrence, H, R$^{2c}$, C$_1$-C$_6$ alkyl substituted with 1 R$^{2c}$, C$_1$-C$_8$ alkyl substituted with 0-3 R$^{2d}$, C$_2$-C$_6$ alkenyl substituted with 0-3 R$^{2d}$, or C$_2$-C$_6$ alkynyl substituted with 0-3 R$^{2d}$;

R$^{2b}$ is, independently at each occurrence, H, C$_1$-C$_3$ alkyl or phenyl;

R$^{2c}$ is, independently at each occurrence, C$_3$-C$_{13}$ mono- or bicycloalkyl substituted with 0-3 R$^{2e}$, C$_6$-C$_{10}$ aryl substituted with 0-3 R$^{2e}$, or 5-14 membered unsaturated, partially unsaturated or saturated heterocyclyl consisting of carbon atoms and 1-4 heteratoms independently chosen from O, N, and S, and substituted with 0-3 R$^{2e}$;

R$^{2d}$ is, independently at each occurrence, halogen, —CF$_3$, C$_1$-C$_6$ alkyl, C$_1$-C$_6$ alkoxy, —CN, —NO$_2$, =O, —OR$^{2f}$, —OC(O)R$^{2f}$, —OC(O)OR$^{2f}$, —OC(O)NR$^{2b}$R$^{2f}$, —NR$^{2b}$R$^{2f}$, —NR$^{2b}$C(O)R$^{2f}$, —NR$^{2b}$C(O)OR$^{2f}$, —NR$^{2b}$C(O)NR$^{2b}$R$^{2f}$, —NR$^{2b}$S(O)$_2$R$^{2f}$, —NR$^{2b}$S(O)$_2$NR$^{2b}$R$^{2f}$, —C(O)R$^{2f}$—C(O)OR$^{2f}$, —C(O)NR$^{2b}$R$^{2f}$, —C(O)NHS(O)$_2$R$^{2f}$, —S(O)$_2$NHC(O)R$^{2f}$, or —C(O)NHC(O)R$^{2f}$;

R$^{2e}$ is, independently at each occurrence, halogen, —CF$_3$, C$_1$-C$_6$ alkyl, C$_1$-C$_6$ alkoxy, —CN, —NO$_2$, =O, —OR$^{2f}$, —OC(O)R$^{2f}$, —OC(O)OR$^{2f}$—OC(O)NR$^{2b}$R$^{2f}$, —NR$^{2b}$R$^{2f}$, —NR$^{2b}$C(O)R$^{2f}$, —NR$^{2b}$C(O)OR$^{2f}$, —NR$^{2b}$C(O)NR$^{2b}$R$^{2f}$, —NR$^{2b}$S(O)$_2$R$^{2f}$, —NR$^{2b}$S(O)$_2$NR$^{2b}$R$^{2f}$, —C(O)R$^{2f}$, —C(O)OR$^{2f}$, —C(O)NR$^{2b}$R$^{2f}$, —C(O)NHS(O)$_2$R$^{2f}$, —S(O)$_2$NHC(O)R$^{2f}$, or —C(O)NHC(O)R$^{2f}$;

R$^{2f}$ is, independently at each ocurrence, H, C$_1$-C$_6$ alkyl, phenyl, benzyl, or CF$_3$;

R$^3$ is H, F, or CH$_3$;

R$^4$ is H, F, or CH$_3$;

alternatively, R$^3$ and R$^4$ are taken together to form —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;

R$^5$ is selected from:

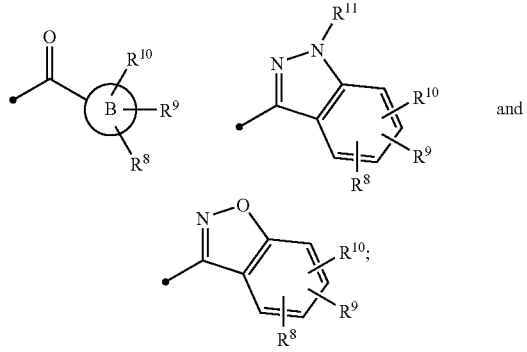

ring B is C$_6$-C$_{10}$ aryl or 5-10 membered heteroaryl consisting of carbon atoms and 0-4 heteratoms independently selected from N, O, and S;

R$^6$ is, independently at each ocurrence, H, C$_1$-C$_3$ alkyl, halogen, —CF$_3$, —OH, C$_1$-C$_3$ alkoxy, —OCF$_3$, —CN, —NO$_2$, —C(=O)NH$_2$, —NH$_2$, —NH(C$_1$-C$_3$ alkyl), or —N(C$_1$-C$_3$ alkyl)$_2$;

R$^7$ is H, C$_1$-C$_6$ alkyl, phenyl, benzyl, or phenethyl;

R$^8$ is, independently at each ocurrence, H, halogen, —CF$_3$, C$_1$-C$_6$ alkyl, C$_1$-C$_6$ alkoxy, —CN, —NO$_2$, —OR$^{2f}$, —OC(O)R$^{2f}$, —OC(O)OR$^{2f}$, —OC(O)NR$^{2b}$R$^{2f}$, —NR$^{2b}$R$^{2f}$, —NR$^{2b}$C(O)R$^{2f}$, —NR$^{2b}$C(O)OR$^{2f}$, —NR$^{2b}$C(O)NR$^{2b}$R$^{2f}$, —NR$^{2b}$S(O)$_2$R$^{2f}$, —NR$^{2b}$S(O)$_2$NR$^{2b}$R$^{2f}$, —C(O)R$^{2f}$, —C(O)OR$^{2f}$, —C(O)NR$^{2b}$R$^{2f}$, —C(O)NHS(O)$_2$R$^{2f}$, —S(O)$_2$NHC(O)R$^{2f}$, or —C(O)NHC(O)R$^{2f}$;

R$^9$ is, independently at each ocurrence, H, halogen, —CF$_3$, C$_1$-C$_6$ alkyl, C$_1$-C$_6$ alkoxy, —CN, —NO$_2$, —OR$^{2f}$, —OC(O)R$^{2f}$, —OC(O)OR$^{2f}$, —OC(O)NR$^{2b}$R$^{2f}$, —NR$^{2b}$R$^{2f}$, —NR$^{2b}$C(O)R$^{2f}$, —NR$^{2b}$C(O)OR$^{2f}$, —NR$^{2b}$C(O)NR$^{2b}$R$^{2f}$, —NR$^{2b}$S(O)$_2$R$^{2f}$, —NR$^{2b}$S(O)$_2$NR$^{2b}$R$^{2f}$, —C(O)R$^{2f}$, —C(O)OR$^{2f}$, —C(O)NR$^{2b}$R$^{2f}$, —C(O)NHS(O)$_2$R$^{2f}$, —S(O)$_2$NHC(O)R$^{2f}$, or —C(O)NHC(O)R$^{2f}$;

R$^{10}$ is, independently at each ocurrence, H, halogen, —CF$_3$, C$_1$-C$_6$ alkyl, C$_1$-C$_6$ alkoxy, —CN, —NO$_2$, —OR$^{2f}$, —OC(O)R$^{2f}$, —OC(O)OR$^{2f}$, —OC(O)NR$^{2b}$R$^{2f}$, NR$^{2b}$R$^{2f}$, —NR$^{2b}$C(O)R$^{2f}$, —NR$^{2b}$C(O)OR$^{2f}$, —NR$^{2b}$C(O)NR$^{2b}$R$^{2f}$, —NR$^{2b}$S(O)$_2$R$^{2f}$, —NR$^{2b}$S(O)$_2$NR$^{2b}$R$^{2f}$, —C(O)R$^{2f}$, —C(O)OR$^{2f}$, —C(O)NR$^{2b}$R$^{2f}$, —C(O)NHS(O)$_2$R$^{2f}$, —S(O)$_2$NHC(O)R$^{2f}$, or —C(O)NHC(O)R$^{2f}$;

alternatively, R$^8$ and R$^9$, or R$^9$ and R$^{10}$ may be combined and, together with the carbon atom to which they are attached, they form a 4-14 membered fully unsaturated or partially unsaturated carbocyclic or heterocyclic ring consisting of: carbon atoms and 0-4 heteratoms independently selected from O, N, and S, and substituted with 0-2 R$^{2e}$; and R$^{11}$ is H, C$_1$-C$_6$ alkyl, —CO(C$_1$-C$_6$ alkyl), —SO$_2$-phenyl, or —SO$_2$—(C$_1$-C$_6$ alkyl);

provided that:

(i) when A is phenyl, B is phenyl, and X is O, then R$^2$ is other than H, C$_1$-C$_3$ alkyl, carboxy-C$_1$-C$_3$ alkyl, C$_1$-C$_4$ alkoxy-CO—, C$_1$-C$_4$ alkoxy-CO—C$_1$-C$_3$ alkyl, or phenyl-C$_1$-C$_3$ alkyl;

(ii) when A is phenyl, B is phenyl, and X is NR$^7$, then R$^2$ is other than H or C$_1$-C$_3$ alkyl.

In some embodiments according to the first aspect, the present invention includes compounds of Formula (I) where X is NR$^7$. In other embodiments, the present invention includes compounds of Formula (I) where X is O.

In some embodiments according to the first aspect, the present invention includes compounds of Formula (I) where R$^1$ is —CH$_2$NH$_2$ or —C(=NH) NH$_2$. In other embodiments, R$^1$ is —CH$_2$NH$_2$. In other embodiments, R$^1$ is —C(=NH) NH$_2$.

In some embodiments according to the first aspect, the present invention includes compounds of Formula (I) where R$^2$ is R$^{2c}$, C$_1$-C$_6$ alkyl substituted with 0-2 R$^{2d}$, C$_2$-C$_4$ alkenyl substituted with 0-2 R$^{2d}$, C$_2$-C$_4$ alkynyl substituted with 0-2 R$^{2d}$, —(CH$_2$)$_{0-3}$C(O)R$^{2a}$, —(CH$_2$)$_{0-3}$C(O)OR$^{2a}$, —(CH$_2$)$_{0-3}$C(O)NR$^{2b}$R$^{2a}$, —(CH$_2$)$_{0-3}$SO$_2$R$^{2a}$, —(CH$_2$)$_{0-3}$NR$^{2b}$C(O)R$^{2a}$, —(CH$_2$)$_{0-3}$NR$^{2b}$S(O)$_2$R$^{2a}$, or —(CH$_2$)$_{0-3}$S(O)$_2$N$^{2b}$R$^{2a}$. In other embodiments, R$^2$ is C$_4$-C$_6$ alkyl, C$_1$-C$_6$ alkyl substituted with 1 R$^{2d}$, C$_3$-C$_8$ cycloalkyl, —(CH$_2$)$_{0-3}$-phenyl substituted with 0-2 R$^{2e}$, —(CH$_2$)$_{0-3}$C(O)R$^{2a}$, —(CH$_2$)$_{0-3}$C(O)OR$^{2a}$, —(CH$_2$)$_{0-3}$C(O)NR$^{2b}$R$^{2a}$, —SO$_2$R$^{2a}$, —(CH$_2$)$_{0-3}$OR$^{2a}$, —(CH$_2$)$_{0-3}$NR$^{2b}$C(O)R$^{2a}$, —(CH$_2$)$_{0-3}$NR$^{2b}$C(O)OR$^{2a}$, —(CH$_2$)$_{0-3}$NR$^{2b}$C(O)NR$^{2b}$R$^{2a}$, or —(CH$_2$)$_{0-3}$NR$^{2b}$S(O)$_2$R$^{2a}$. In other embodiments, R$^2$ is C$_1$-C$_6$ alkyl substituted with 0-1 R$^{2d}$, C$_3$-C$_8$ cycloalkyl, phenyl-(CH$_2$)$_{0-3}$— substituted with 0-2 R$^{2e}$, —(CH$_2$)$_{0-3}$C(=O)R$^{2a}$, —(CH$_2$)$_{0-3}$C(=O)OR$^{2a}$, —(CH$_2$)$_{0-3}$C(=O)NR$^{2b}$R$^{2a}$, or —SO$_2$R$^{2a}$. In further embodiments, R$^2$ is butyl, i-butyl, s-butyl, t-butyl, cyclopentyl, —CH$_2$CONH(cyclopentyl), cyclohexyl, —CH$_2$CONH(cyclohexyl), —CH$_2$CON(CH$_3$)(cyclohexyl), phenyl, —CONHPh, —CH$_2$CONHPh, —CH$_2$CON(Me)HPh, —CH$_2$CONH(2-

Me-Ph), —CH$_2$CONH(3-Me-Ph), —CH$_2$CONH(4-Me-Ph), —CH$_2$CONH(2-F-Ph), —CH$_2$CONH(3-F-Ph), —CH$_2$CONH(4-F-Ph), —CH$_2$CONH(2-OMe-Ph), —CH$_2$CONH(3-OMe-Ph), —CH$_2$CONH(4-OMe-Ph), benzyl, 3-CO$_2$H-benzyl, 4-CO$_2$H-benzyl, —CObenzyl, phenethyl, phenylpropyl, —CH$_2$-CONH(2-pyridyl), —CH$_2$—CONH(3-pyridyl), —CH$_2$—CONH(4-pyridyl), —CH$_2$CONH(2-thiazolyl), —CH$_2$CONH(2-Me-2H-3-pyrazolyl), —CH$_2$CO$_2$H, —(CH$_2$)$_2$CO$_2$H, —CO$_2$Me, —SO$_2$Me, —CH$_2$CH$_2$OMe, —CH$_2$CH$_2$OPh, —CH$_2$CH$_2$NH$_2$, —CH$_2$CH$_2$NHCOMe, —CH$_2$CH$_2$NHCOPh, —CH$_2$CONH$_2$, —CH$_2$CONHMe, —CH$_2$CH$_2$NHCO$_2$Me, —CH$_2$CH$_2$NHCONHMe, —CH$_2$CH$_2$OH, —CH$_2$CH$_2$O(benzyl), —CH$_2$CH$_2$NHSO$_2$Me, —CH$_2$CH$_2$CONHMe, —CH$_2$CH$_2$CONHPh, 3-CO$_2$H-Ph, or 4-CO$_2$H-Ph.

In some embodiments according to the first aspect, the present invention includes compounds of Formula (I) where R$^3$ is H or CH$_3$. In other embodiments, R$^3$ is H.

In some embodiments according to the first aspect, the present invention includes compounds of Formula (I) where R$^4$ is H or CH$_3$. In other embodiments, R$^4$ is H.

In some embodiments according to the first aspect, the present invention includes compounds of Formula (I) where R$^5$ is

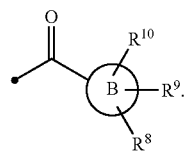

In other embodiments, R$^5$ is

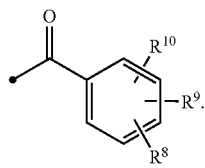

In some embodiments according to the first aspect, the present invention includes compounds of Formula (I) where R$^5$ is

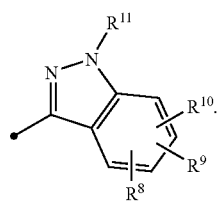

In some embodiments according to the first aspect, the present invention includes compounds of Formula (I) where R$^5$ is

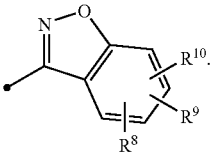

In some embodiments according to the first aspect, the present invention includes compounds of Formula (I) where R$^6$ is H, C$_1$-C$_3$ alkyl, F, Cl, Br, —CF$_3$, —OH, C$_1$-C$_3$ alkoxy, or —OCF$_3$.

In some embodiments according to the first aspect, the present invention includes compounds of Formula (I) where R$^7$ is H, C$_1$-C$_4$ alkyl, phenyl, benzyl, or phenethyl. In othe embodiments, where R$^7$ is H, Me, Et, Pr, i-Pr, Bu, i-Bu, phenyl, benzyl, or phenethyl. In further embodiments, R$^7$ is H Me, or phenethyl.

In some embodiments according to the first aspect, the present invention includes compounds of Formula (I) where R$^8$, R$^9$, R$^{10}$ are, independently at each occurrence, H, C$_1$-C$_3$ alkyl, F, Cl, Br, —CF$_3$, —OH, C$_1$-C$_3$ alkoxy, or —OCF$_3$. In other embodiments, where R$^8$, R$^9$, R$^{10}$ are, independently at each occurrence, H, Me, Et, —OH, —OMe, or —OEt. In further embodiments, R$^8$, R$^9$, R$^{10}$ are, independently at each occurrence, H, Me, Et, OMe, OH, Cl, CF$_3$, or OCF$_3$.

In some embodiments according to the first aspect, the present invention includes compounds of Formula (I) where R$^{11}$ is H, C$_1$-C$_4$ alkyl, —CO(C$_1$-C$_4$ alkyl), —SO$_2$phenyl, or —SO$_2$(C$_1$-C$_4$ alkyl).

In a second aspect, the present invention includes compounds of Formula (I) or a stereoisomer or pharmaceutically acceptable salt, solvate, or prodrug form thereof, wherein:

each R$^{1c}$ is, independently at each occurrence, H, —OH, —OR$^{1e}$, —C(O)OR$^{1e}$, —OC(O)R$^{1e}$, —OS(O)$_2$R$^{1e}$, —NH$_2$, —NR$^{1a}$R$^{1e}$, —NR$^{1a}$C(O)R$^{1e}$, —NR$^{1a}$C(O)R$^{1a}$R$^{1e}$, —C(O)R$^{1e}$, —CH$_2$OC(O)R$^{1e}$, —S(O)$_2$R$^{1e}$, or —C(O)SR$^{1e}$;

each R$^{1d}$ is, independently at each occurrence, H, —OH, —OR$^{1e}$, —C(O)OR$^{1e}$, —OC(O)R$^{1e}$, —OS(O)$_2$R$^{1e}$, —NH$_2$, —NR$^{1a}$R$^{1e}$, —NR$^{1a}$C(O)R$^{1e}$, —NR$^{1a}$C(O)R$^{1a}$R$^{1e}$, —C(O)R$^{1e}$, —CH$_2$OC(O)R$^{1e}$, —S(O)$_2$R$^{1e}$, or —C(O)SR$^{1e}$; and each R$^{1e}$ is, independently at each occurrence, C$_1$-C$_4$ alkyl substituted with 0-3 R$^{1g}$, C$_2$-C$_4$ alkenyl substituted with 0-3 R$^{1g}$, C$_2$-C$_4$ alkynyl substituted with 0-3 R$^{1g}$, or phenyl substituted with 0-3 R$^{1g}$.

In a third aspect, the present invention includes compounds of Formula (I) or a stereoisomer or pharmaceutically acceptable salt, solvate, or prodrug form thereof, wherein:

ring A is phenyl substituted with 0-2 R$^6$ or pyridyl substituted with 0-2 R$^6$;

X is NR$^7$;

R$^3$ is H, F, or CH$_3$;

R$^4$ is H, F, or CH$_3$;

R$^5$ is selected from:

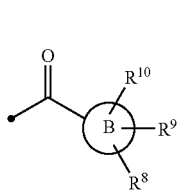 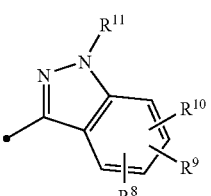 and

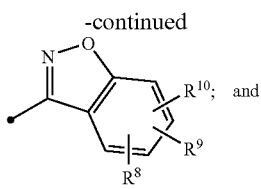

ring B is phenyl or 5-6 membered heteroaryl consisting of carbon atoms and 0-2 heteroatoms independently selected from N, O, and S; and $R^{11}$ is H, $C_1$-$C_4$ alkyl, —CO($C_1$-$C_4$ alkyl), —$SO_2$-phenyl, or —$SO_2$—($C_1$-$C_4$ alkyl);

provided that when when A is phenyl and B is phenyl, then $R^2$ is other than H or $C_1$-$C_3$ alkyl.

In a fourth aspect, the present invention includes compounds of Formula (I) or a stereoisomer or pharmaceutically acceptable salt, solvate, or prodrug form thereof, wherein:

ring A is phenyl substituted with 0-1 $R^6$;

$R^1$ is —$CH_2NH_2$, —$CH_2NH(C_1$-$C_4$ alkyl), —$CH_2N(C_1$-$C_4$ alkyl)$_2$, or —C(=NH)$NH_2$;

X is $NR^7$;

$R^3$ is H or $CH_3$;

$R^4$ is H, or $CH_3$;

$R^5$ is

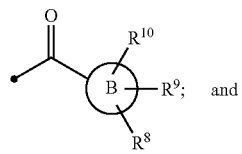

$R^7$ is H, $C_1$-$C_4$ alkyl, benzyl, or phenethyl.

In a fifth aspect, the present invention includes compounds of Formula (I) or a stereoisomer or pharmaceutically acceptable salt, solvate, or prodrug form thereof, wherein:

$R^2$ is $C_4$-$C_6$ alkyl, $C_1$-$C_6$ alkyl substituted with 1 $R^{2d}$, $C_3$-$C_8$ cycloalkyl, —$(CH_2)_{0-3}$-phenyl substituted with 0-2 $R^{2e}$, —$(CH_2)_{0-3}C(O)R^{2a}$, —$(CH_2)_{0-3}C(O)OR^{2a}$, —$(CH_2)_{0-3}C(O)NR^{2b}R^{2a}$, —$SO_2R^{2a}$, —$(CH_2)_{0-3}OR^{2a}$, —$(CH_2)_{0-3}NR^{2b}C(O)R^{2a}$, —$(CH_2)_{0-3}NR^{2b}C(O)OR^{2a}$, —$(CH_2)_{0-3}NR^{2b}C(O)NR^{2b}R^{2a}$, or —$(CH_2)_{0-3}NR^{2b}S(O)_2R^{2a}$; and $R^{2a}$ is, independently at each occurrence, H, $C_1$-$C_4$ alkyl substituted with 0 to 1 $R^{2d}$, $C_3$-$C_6$ cycloalkyl substituted with 0-1 $R^{2e}$, phenyl substituted with 0 to 1 $R^{2e}$, benzyl substituted with 0-1 $R^{2e}$, or 5-6 membered heteroaryl substituted with 0-1 $R^{2e}$.

In a sixth aspect, the present invention includes the compounds of Formula (I), or a stereoisomer or pharmaceutically acceptable salt, solvate, or prodrug form thereof, wherein:

ring A is phenyl;

X is NH;

$R^1$ is —C(=NH)$NH_2$ or —$CH_2NH_2$;

$R^3$ is H;

$R^4$ is H; and $R^5$ is

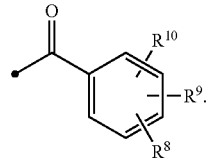

In a seventh aspect, the present invention includes the compounds of Formula (I), or a stereoisomer or pharmaceutically acceptable salt, solvate, or prodrug form thereof, wherein:

ring A is phenyl;

$R^1$ is —C(=NH)$NH_2$, or $CH_2NH_2$;

$R^2$ is butyl, i-butyl, s-butyl, t-butyl, cyclopentyl, —$CH_2$CONH(cyclopentyl), cyclohexyl, —$CH_2$CONH(cyclohexyl), —$CH_2$CON($CH_3$)(cyclohexyl), phenyl, —CONHPh, —$CH_2$CONHPh, —$CH_2$CON(Me)HPh, —$CH_2$CONH(2-Me-Ph), —$CH_2$CONH(3-Me-Ph), —$CH_2$CONH(4-Me-Ph), —$CH_2$CONH(2-F-Ph), —$CH_2$CONH(3-F-Ph), —$CH_2$CONH(4-F-Ph), —$CH_2$CONH(2-OMe-Ph), —$CH_2$CONH(3-OMe-Ph), —$CH_2$CONH(4-OMe-Ph), benzyl, 3-CO2H-benzyl, 4-$CO_2$H-benzyl, —CObenzyl, phenethyl, phenylpropyl, —$CH_2$—CONH(2-pyridyl), —$CH_2$—CONH(3-pyridyl), —$CH_2$—CONH(4-pyridyl), —$CH_2$CONH(2-thiazolyl), —$CH_2$CONH(2-Me-2H-3-pyrazolyl), —$CH_2CO_2$H, —$(CH_2)_2CO_2$H, —$CO_2$Me, —$SO_2$Me, —$CH_2CH_2$OMe, —$CH_2CH_2$OPh, —$CH_2CH_2NH_2$, —$CH_2CH_2$NHCOMe, —$CH_2CH_2$NHCOPh, —$CH_2$CONH$_2$, —$CH_2$CONHMe, —$CH_2CH_2$NHCO$_2$Me, —$CH_2CH_2$NHCONHMe, —$CH_2CH_2$OH, —$CH_2CH_2$O(benzyl), —$CH_2CH_2$NHSO$_2$Me, —$CH_2CH_2$CONHMe, —$CH_2CH_2$CONHPh, 3-$CO_2$H-Ph, or 4-$CO_2$H-Ph; and $R^8$, $R^9$, and $R^{10}$ are, independently at each occurrence, H, Me, Et, OMe, OH, Cl, $CF_3$, or $OCF_3$.

In an eighth aspect, the present invention provides a compound selected from Examples 1-69 or a stereoisomer or a pharmaceutically acceptable salt, solvate, or prodrug form thereof.

In another embodiment, the present invention provides a novel process for making a compound of the present invention or a stereoisomer or a pharmaceutically acceptable salt, solvate, or prodrug form thereof.

In another embodiment, the present invention provides a novel intermediate for making a compound of the present invention or a stereoisomer or a pharmaceutically acceptable salt, solvate, or prodrug form thereof.

In another embodiment the present invention provides a pharmaceutical composition comprising a pharmaceutically acceptable carrier and a therapeutically effective amount of at least one of the compounds of the present invention or a stereoisomer or a pharmaceutically acceptable salt, solvate, or prodrug form thereof.

In another embodiment the present invention provides a method for modulation of the coagulation cascade and/or contact activation system comprising administering to a patient in need of such treatment a therapeutically effective amount of at least one of the compounds of the present invention or a stereoisomer or a pharmaceutically acceptable salt, solvate, or prodrug form thereof.

In another embodiment the present invention provides a method for treating thromboembolic disorders comprising:

administering to a patient in need of such treatment a therapeutically effective amount of at least one of the compounds of the present invention or a stereoisomer or a pharmaceutically acceptable salt, solvate, or prodrug form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a stereoisomer or a pharmaceutically acceptable salt, solvate, or prodrug form thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a novel method of treating a patient in need of thromboembolic disorder treatment, comprising: administering a compound of the present invention or a stereoisomer or a pharmaceutically acceptable salt, solvate, or prodrug form thereof in an amount effective to treat a thromboembolic disorder.

In another embodiment, the present invention provides a method of treating a patient in need of inflammatory disorder treatment, comprising: administering a compound of the present invention or a stereoisomer or a pharmaceutically acceptable salt, solvate, or prodrug form thereof in an amount effective to treat an inflammatory disorder.

In another embodiment, the present invention provides a method, comprising: administering a compound of the present invention or a stereoisomer or a pharmaceutically acceptable salt, solvate, or prodrug form thereof in an amount effective to treat a thromboembolic and/or inflammatory disorder.

In another embodiment, the present invention provides a pharmaceutical composition further comprising at least one additional herapeutic agent selected from one or more of potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In a preferred embodiment, the present invention provides a pharmaceutical composition wherein the additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithirombotic agent selected from anticoagulants selected from thrombin inhibitors, other factor VIIa inhibitors, other plasma kallikrein inhibitors, factor VIIa inhibitors and factor Xa inhibitors, and antiplatelet agents selected from GPIIb/IIIa blockers, $P2Y_1$ and $P2Y_{12}$ antagonists, thromboxane receptor antagonists, and aspirin, or a combination thereof.

In a preferred embodiment, the present invention provides a pharmaceutical composition, wherein the additional therapeutic agent(s) are an anti-platelet agent or a combination thereof.

In a preferred embodiment, the present invention provides a pharmaceutical composition, wherein the additional therapeutic agent is an anti-platelet agent selected from clopidogrel and/or aspririn.

In another embodiment, the present invention provides a method of treating a Factor VIIa-associated disorder comprising administering an effective amount of at least one compound of the present invention, or a stereoisomer or a pharmaceutically acceptable salt or solvate thereof, to a patient in need thereof.

In another embodiment, the present invention provides a method of treating a Factor VIIa-associated disorder, wherein the Factor VIIa-associated disorder is selected from myocardial infarction, coronary artery disease, non-Q wave MI, congestive heart failure, cardiac arrhythmias, unstable angina, chronic stable angina, Prinzmetal's angina, high blood pressure, intermittent claudication, and peripheral occlusive arterial disease.

In another embodiment, the present invention provides a novel method, comprising: administering a compound of the present invention or a stereoisomer or a pharmaceutically acceptable salt, solvate, or prodrug form thereof in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a stereoisomer or a pharmaceutically acceptable salt, solvate, or prodrug form thereof; and, (c) a package insert stating that the pharmaceutical composition can be used for the treatment of a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a stereoisomer or a pharmaceutically acceptable salt, solvate, or prodrug form thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Thus, the stereoisomeric configurations of each compound are considered part of the invention.

Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

When any variable (e.g., $R^{2b}$, $R^{8b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$-$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

"Alkoxy" or "alkyloxy" represents an alkyl group as defined above with the indicated number of carbon atoms attached through an oxygen bridge. For example, "$C_1$-$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane(decalin), [2.2.2] bicyclooctane, fluorenyl, phenyl, naphthyl, indanyl, adamantyl, or tetrahydronaphthyl(tetralin). Preferred carbocycles, unless otherwise specified, are cyclopropyl, cyclobutyl, cyclopentyl, cyclohexyl, phenyl, and indanyl.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2, 5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2, 4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydro-benzofuranyl, chromanyl, 1,2,3,4-tetrahydro-quinoxaline, and 1,2,3,4-tetrahydro-quinazoline.

As used herein, the term "bicyclic carbocycle" or "bicyclic carbocyclic group" is intended to mean a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "aryl", "$C_6$-$C_{10}$ aryl" or "aromatic residue", is intended to mean an aromatic moiety containing, if specified, the specified number of carbon atoms; for example phenyl or naphthyl. Unless otherwise specified, "aryl", "$C_6$-$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized. It is to be noted that total number of S and O atoms in the aromatic heterocycle is not more than 1.

The term "counterion" is used to represent a small, negatively charged species such as chloride, bromide, hydroxide, acetate, and sulfate.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "*Design and Application of Prodrugs*," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor VIIa and/or plasma kallikrein. "Therapeutically effective amount" is also intended to include an amount of the combination of compounds claimed that is effective to inhibit factor VIIa and/or plasma kallikrein. The combination of compounds is preferably a synergistic combination. Synergy, as described, for example, by Chou and Talalay, *Adv. Enzyme Regul.* 1984, 22:27-55, occurs when the effect (in this case, inhibition of factor VIIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3nd Edition, 1999). All references cited herein are hereby incorporated in their entirety herein by reference.

Schemes 1, 2, and 5 describe synthetic routes to compounds of the invention. The starting materials for these synthetic routes are either commercially available or may be prepared by methods known to one skilled in the art of organic synthesis from commercially available materials. In these schemes, $R^1$ indicates amidine or aminomethyl, protected amidine or aminomethyl, or precursor to amidine or aminomethyl such as nitrile or halogen. These $R^1$ substituents may be interconverted as necessary at appropriate positions in the synthetic schemes by a wide variety of methods known to one skilled in the art of organic synthesis. Schemes 3 and 4 describe some methods for converting the various precursors or protected derivatives to the amidine and aminomethyl compounds of the invention.

Scheme 1 shows a general synthetic route to compounds of the invention for which $X=NR^7$. Nitro compounds 1.1 are commercially available or may be prepared by methods known to one skilled in the art of organic synthesis. Bromination of the methyl group in compound 1.1 may be effected with N-bromosuccinimide using photochemical initiation or a radical initiator, such as benzoyl peroxide or AIBN. The reaction is performed in a solvent such as carbon tetrachloride or dichloromethane. Alternative brominating agents which may effect this transformation include $Br_2$ and $KBrO_3$. Bromide 1.2 is reacted with potassium pthalimide in a solvent such as DMF to give compound 1.3. Deprotection with hydrazine or methylhydrazine using, for instance, an alcoholic solvent at reflux affords aminomethyl compound 1.4. As an alternative to pthalimide, sodium azide may be reacted with compound 1.2 in a solvent such as DMF to give a benzylic azide intermediate. The azide may be selectively reduced to amino methyl compound 1.4 by several methods, including triphenylphosphine/water and tin(II) benzenethiolate. Carboxylic acids 1.5 are commercially available or may be prepared by methods known to one skilled in the art of organic synthesis. Compound 1.5 and compound 1.4 may be coupled to afford amide 1.6 using one of a wide array of peptide coupling reagents and conditions known to one skilled in the art of organic synthesis. For instance, EDCI and HOAT in a mixture of DMF and dichloromethane. Alternatively, reaction of 1.5 with isobutylchloroformate in the presence of a base such as N-methyl morpholine ("mixed anhydride method"), followed by addition of 1.4 may afford amide 1.6. Selective reduction of the nitro group in 1.6 to give amine 1.7 may be conducted with a wide array of methods, including catalytic hydrogenation, for instance with 10% Pd/C in a solvent such as ethyl acetate, ethanol, or methanol, and optionally in the presence of an acid such as hydrochloric acid, acetic acid, or trifluoroacetic acid. Alternatively, reduction may be effected by a metal, such as iron, in a solvent such as acetic acid, or with tin(II) chloride. Introduction of the $R^2$ substituent on the amino group may be conducted in several ways. Reaction of amine 1.7 with trifluoroacetic anhydride, followed by alkylation of trifluoroacetamide 1.8, and deprotection with potassium carbonate in methanol affords intermediate 1.10. Alternatively, a variety of aldehydes and ketones may be reductively aminated with 1.7 to give 1.10, using, for instance, sodium triacetoxyborohydride or sodium borohydride in a solvent such as methanol, dichloromethane, dichloroethane, or timethylorthoformate. In addition, amine 1.7 may be directly alkylated with various alkylating agents, for instance, benzyl halides, using a base such as potassium carbonate and a solvent such as DMF, to give compound 1.10. Introduction of a second substituent $R^7$ may be accomplished by alkylating compound 1.10 with various alkylating agents, for instance, benzyl halides, using a base such as potassium carbonate and a solvent such as DMF, to give compound 1.11. Manipulation of the $R^1$ group to afford the aminomethyl and amidine compounds of the invention may be accomplished as described in Schemes 3 and 4. These transformations may be inserted in the necessary positions in Scheme 1 as will be appreciated by one skilled in the art. It may also be necessary to perform various transformations, for instance, ester hydrolysis to an acid or amine acylation to an amide, on the $R^2$ and/or $R^7$ substituents to obtain the desired compounds of the invention. These transformations are familiar to one skilled in the art of organic synthesis and may be inserted in the necessary positions in Scheme 1.

Scheme 1

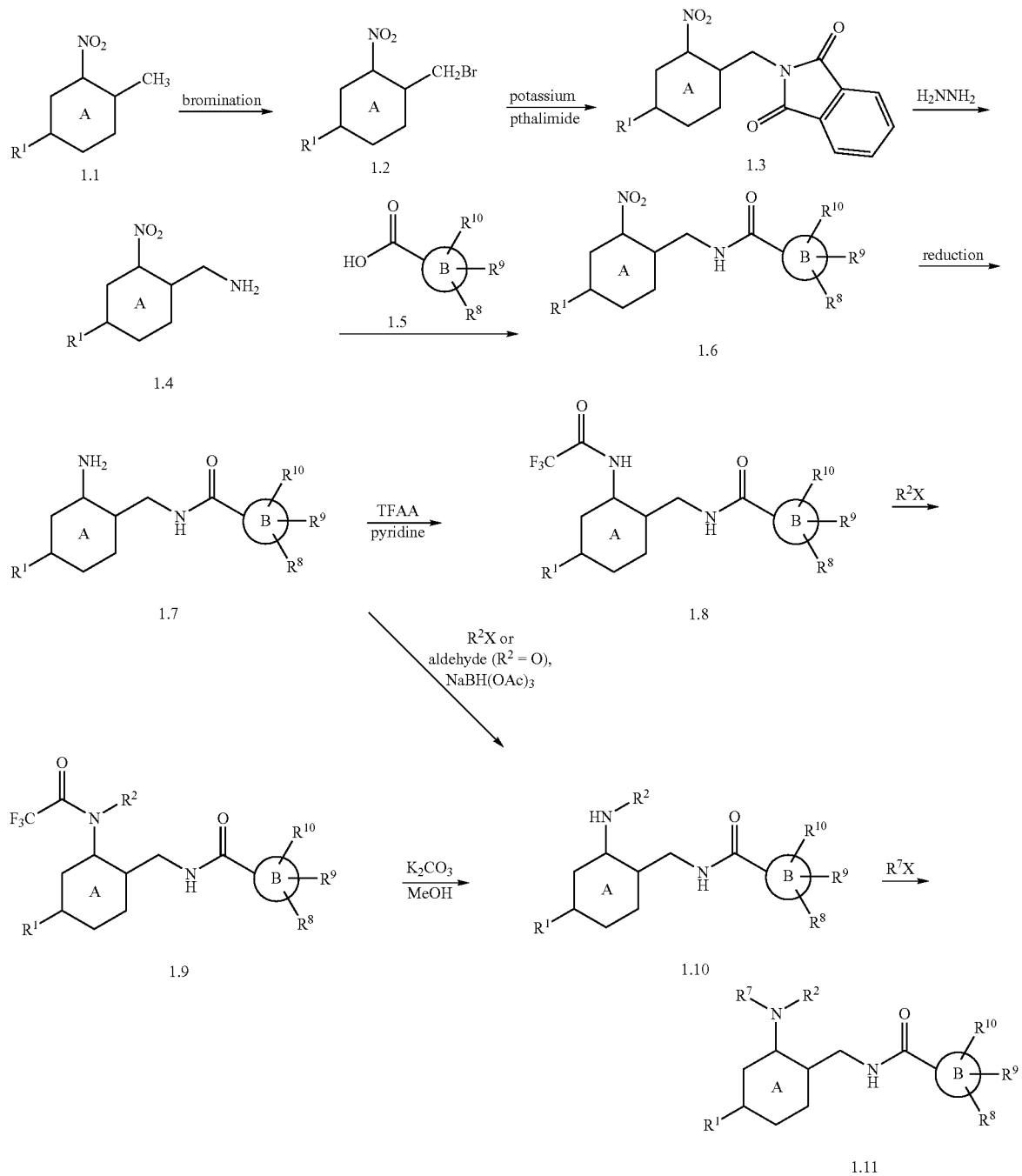

Scheme 2 shows a general synthetic route to compounds of the invention for which X=O. Nitro compounds 2.1 are commercially available or may be prepared by methods known to one skilled in the art of organic synthesis. Selective reduction of the nitro group to give amine 2.2 may be conducted with a wide array of methods, including catalytic hydrogenation, for instance with 10% Pd/C in a solvent such as ethyl acetate, ethanol, or methanol, and optionally in the presence of an acid such as hydrochloric acid, acetic acid, or trifluoroacetic acid. Alternatively, reduction may be effected by a metal, such as iron, in a solvent such as acetic acid, or with tin(II) chloride. Subsequently, the amine 2.2 is diazotized with sodium nitrite in sulfuric acid solution. The intermediate diazonium ion is decomposed with copper(I) oxide and copper(II) nitrate to afford hydroxy compound 2.3. (Cohen, T.; Dietz, A. G.; Miser, J. R. *J. Org. Chem.* 1977, 42, 2053.) Alternative conditions for this transformation include diazotization with alkyl nitrites under nonaqueous conditions and use of other acids, including tetrafluoroboric acid, trifluoroacetic acid, and hydrochloric acid. Protection of the hydroxyl group in 2.3 may be affected with isobutylene in the presence of catalytic sulfuric acid to give t-butyl ether 2.4. Alternative hydroxyl protecting groups may be necessary for particular cases, as will be appreciated by one skilled in the art of organic synthesis. Bromination of the methyl group in compound 2.4 may be effected with N-bromosuccinimide using photochemical initiation or a radical initiator, such as benzoyl peroxide or AIBN. The reaction is performed in a solvent such as carbon tetrachloride or dichloromethane. Alternative brominating agents which may effect this transformation include $Br_2$ and $KBrO_3$. Bromide 2.5 is reacted with potassium pthalimide in a solvent such as DMF to give compound 2.6. Deprotection with hydrazine or methylhydrazine using, for instance, an alcoholic solvent at reflux affords aminomethyl compound 2.7. As an alternative to pthalimide, sodium azide may be reacted with compound 2.5 in a solvent such as DMF to give a benzylic azide intermediate. The azide may be selectively reduced to amino methyl compound 2.7 by several methods, including triphenylphosphine/water and tin(II) benzenethiolate. Carboxylic acids 2.8 are commercially available or may be prepared by methods known to one skilled in the art of organic synthesis. Compound 2.7 and compound 2.8 may be coupled to afford amide 2.9 using one of a wide array of peptide coupling reagents and conditions known to one skilled in the art of organic synthesis. For instance, EDCI and HOAT in a mixture of DMF and dichloromethane. Alternatively, reaction of 2.8 with isobutylchloroformate in the presence of a base such as N-methyl morpholine ("mixed anhydride method"), followed by addition of 2.7 may afford amide 2.9. Subsequent reaction of 2.9 with, for instance, neat trifluoroacetic acid, hydrogen chloride in dioxane, or hydrogen bromide in acetic acid, gives compound 2.10. Introduction of the $R^2$ substituent on the oxygen atom may be conducted in several ways. Hydroxy compound 2.10 may be reacted with isocyanates to form carbamate derivatives 2.11. Alternatively, hydroxy compounds may be reacted with chloroformates in the presence of a base such as TEA to form carbonates 2.11. Hydroxy compound 2.10 may be alkylated with various alkylating reagents, including alkyl, allyl, and benzyl halides, and active heteroaryl halides, using a base such as cesium carbonate in a solvent such as DMF to afford compounds 2.11. Alternative conditions for this transformation include bases such as sodium or potassium hydroxide, additives such as tetrabutylammonium iodide, and phase transfer conditions. Manipulation of the $R^1$ group to afford the aminomethyl and amidine compounds of the invention may be accomplished as described in Schemes 3 and 4. These transformations may be inserted in the necessary positions in Scheme 2 as will be appreciated by one skilled in the art. It may also be necessary to perform various transformations, for instance, ester hydrolysis to an acid or amine acylation to an amide, on the $R^2$ substituent to obtain the desired compounds of the invention. These transformations are familiar to one skilled in the art of organic synthesis and may be inserted in the necessary positions in Scheme 2.

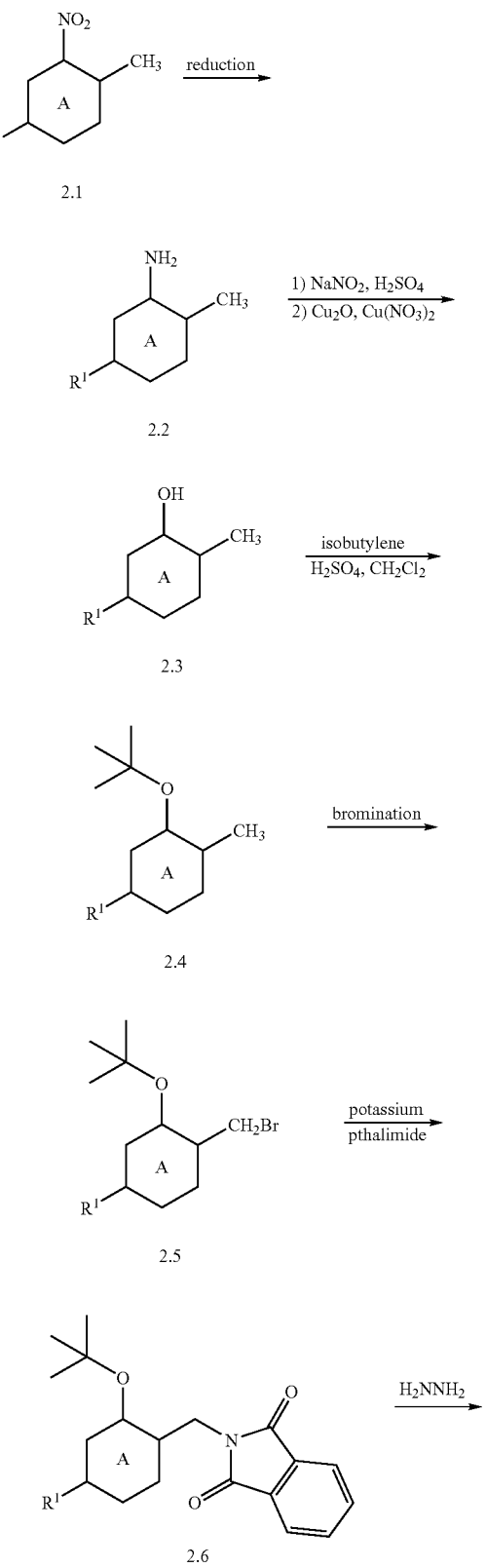

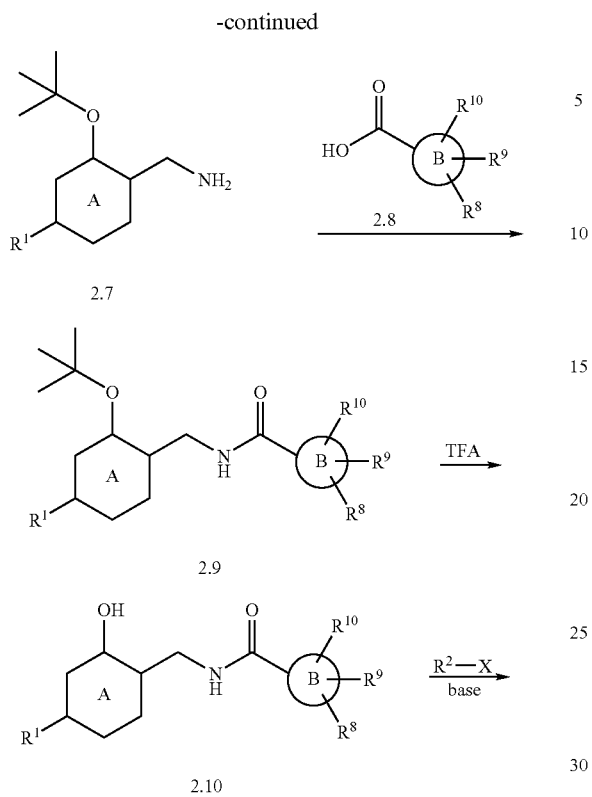

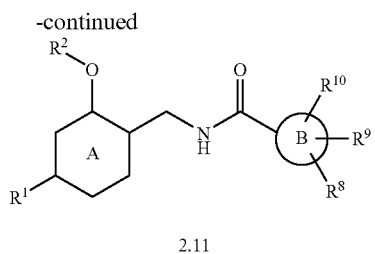

Scheme 3 describes the synthesis of compounds of the invention for which $R^1$=aminomethyl. Note that the functional group shown explicitly for each structure in Scheme 3 is $R^1$. Bromide 3.1 can be converted to nitrile 3.2 using, for instance, zinc(II) cyanide and catalytic Pd(0) in the presence of a phosphine ligand such as triphenylphosphine. Reduction of nitrile 3.2 to amine 3.3 may be achieved with a variety of conditions, including catalytic hydrogenation or hydride reduction with LAH or DIBAH. If necessary, amine 3.3 may be protected as the t-butoxycarbonyl derivative 3.4 by treatment with di-t-butyl dicarbonate. Deprotection of 3.4 with trifluoroacetic acid gives amine 3.3. Alternatively, bromide 3.5 may be converted with sodium azide in DMF to azide 3.6. Subsequent reduction with, for instance, catalytic hydrogenation or triphenylphosphine and water, affords amine 3.3. Another alternative is the reduction of acid derivative 3.7 to alcohol 3.10 and conversion to azide 3.6 under Mitsunobu conditions. Finally, acid derivative 3.7 can be reduced to aldehyde 3.8. Reductive amination gives amine 3.9, which may be deprotected to give amine 3.3.

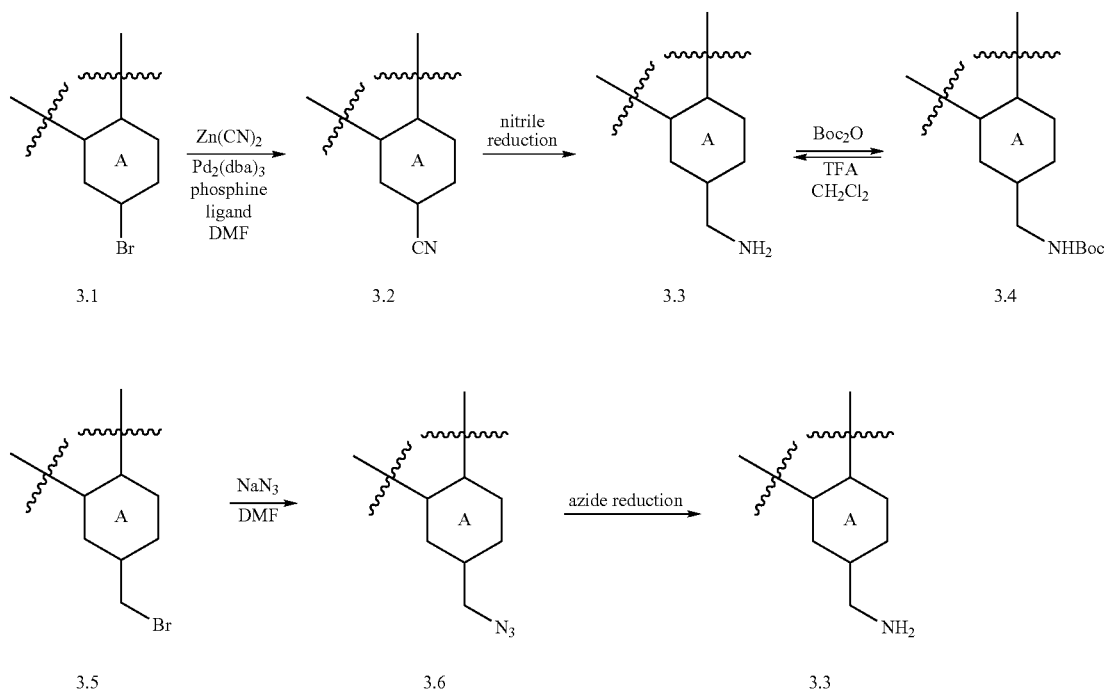

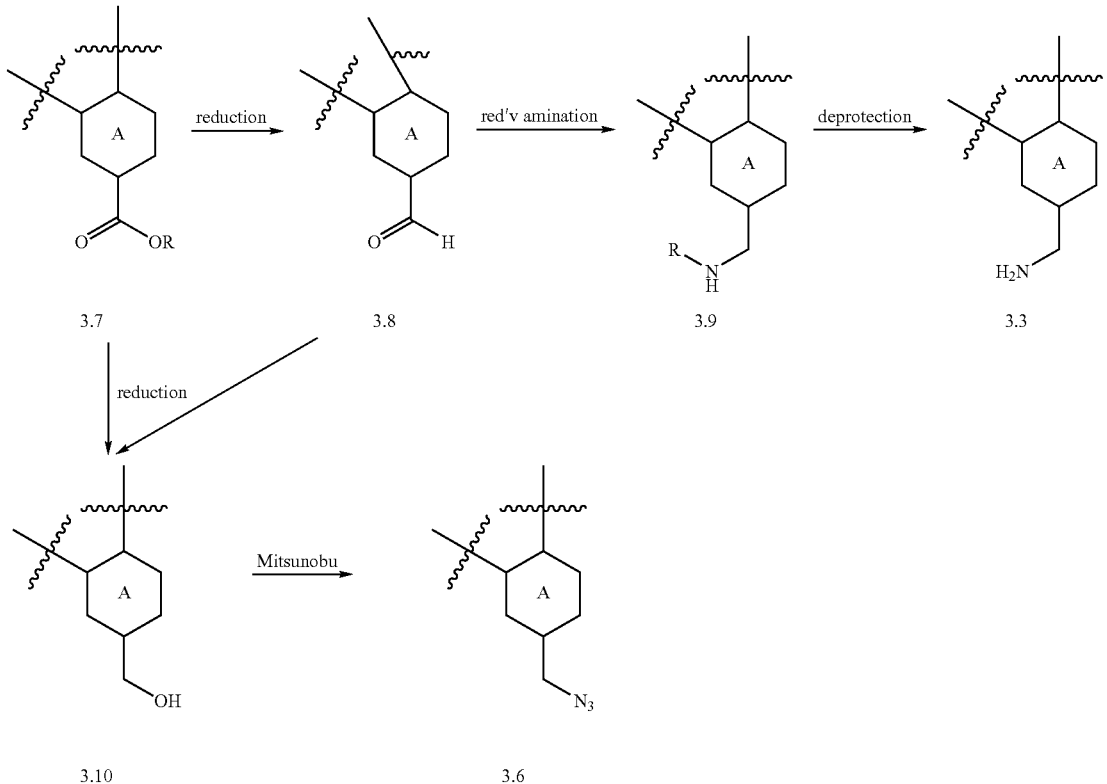

Scheme 4 describes the synthesis of compounds of the invention for which $R^1$=amidine. Note that the functional group shown explicitly for each structure in Scheme 4 is $R^1$. Nitrile 3.2 can be converted to amidine 4.1 by treatment with hydrogen chloride in an alcoholic solvent, followed by treatment with ammonia or ammonium chloride in an alcoholic solvent. If necessary, the amidine may be protected as a carbamate, for instance, by treatment with benzyl chloroformate and base to give compound 4.2. The benzyloxycarbonyl protecting group may be removed by catalytic hydrogenation to afford amidine 4.1. Treatment of nitrile 3.2 with hydroxylamine in dimethyl sulfoxide affords amidoxime 4.3. This compound may be reduced by, for instance Raney nickel and hydrogen, to give amidine 4.1. Alternatively, amidoxime 4.3 may be converted to oxadiazole 4.4, which serves as a convenient and robust protecting group. Subsequent deprotection of amidoxime 4.4, using catalytic hydrogenation, for instance with Raney nickel, affords amidine 4.1.

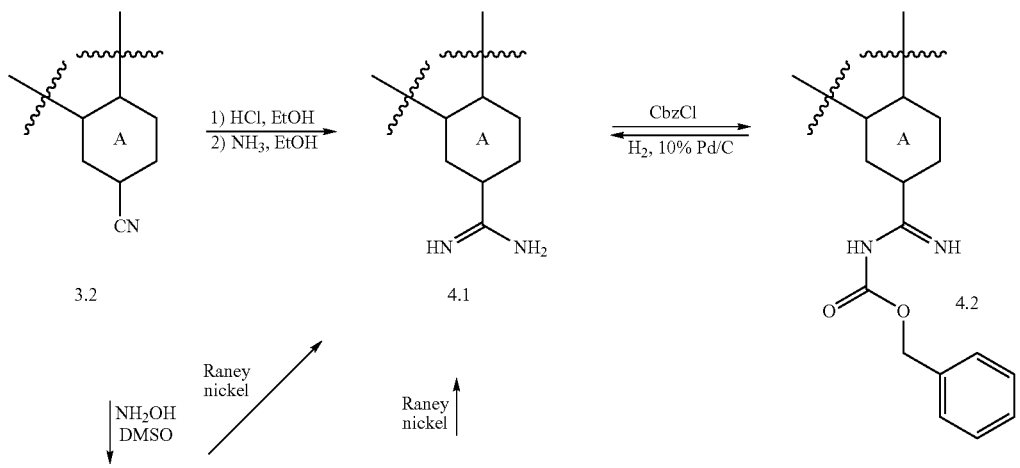

Scheme 4

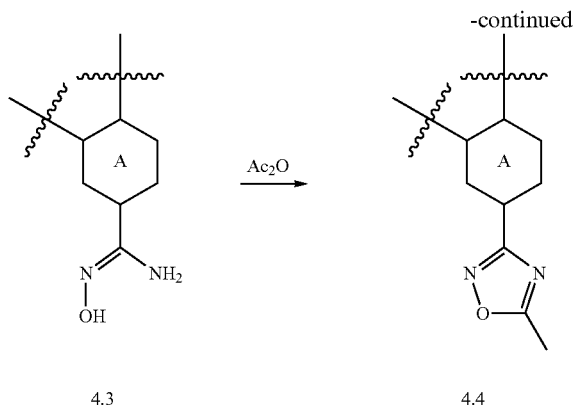

Scheme 5 describes the synthesis of compounds of the innvention with indazole and benzisoxazole $R^5$ groups. Nitriles 5.1 may be prepared by methods known to one skilled in the art of organic synthesis, and may be reacted with hydrazine to afford indazole 5.2. Subsequent alkylation with sodium hydroxide affords indazole 5.3 with an $R^1$ substituent on the ring nitrogen. Compound 5.3 can be linked to aldehyde 5.4 by reductive amination to give indazole 5.5. Subsequent elaboration in analogy with the route described in Scheme 1 gives compound 5.6. Similarly, nitriles 5.1 may be reacted with acetohydroxamic acid in the presence of potassium t-butoxide and DMF to give 3-amino-1,2-benzisoxazole 5.7. Reductive amination with 5.4 and subsequent elaboration of the intermediate 5.8 in analogy with the route described in Scheme 1 affords benzisoxazole 5.9.

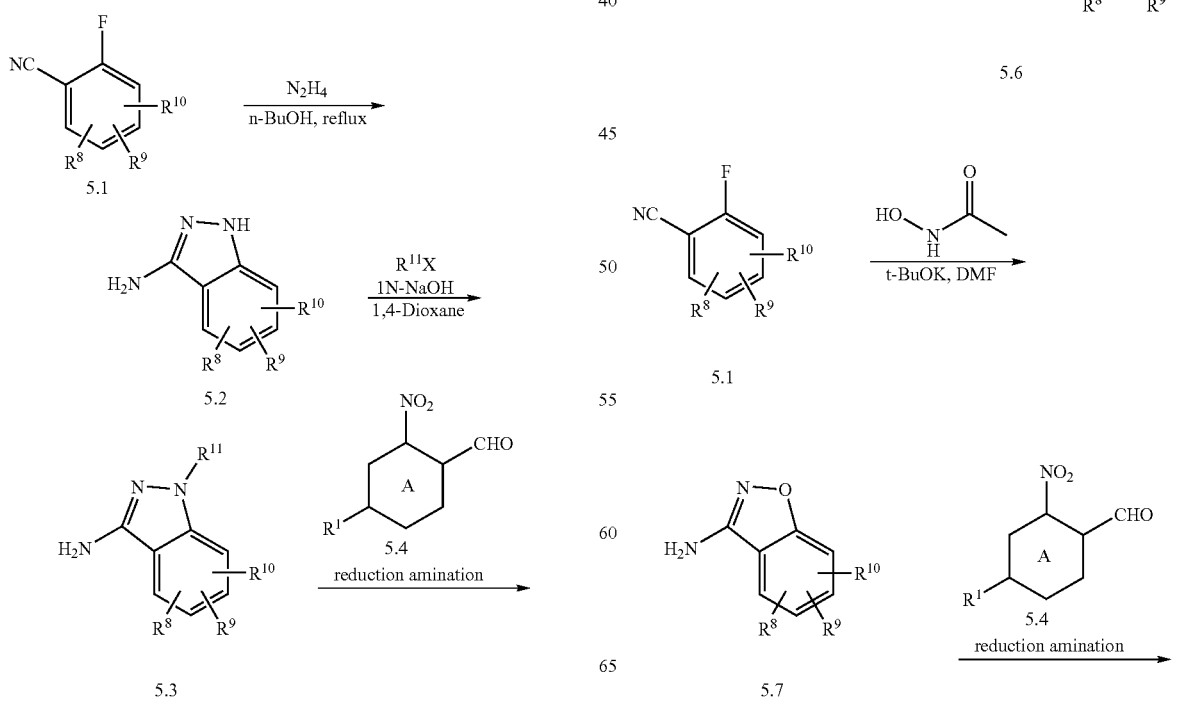

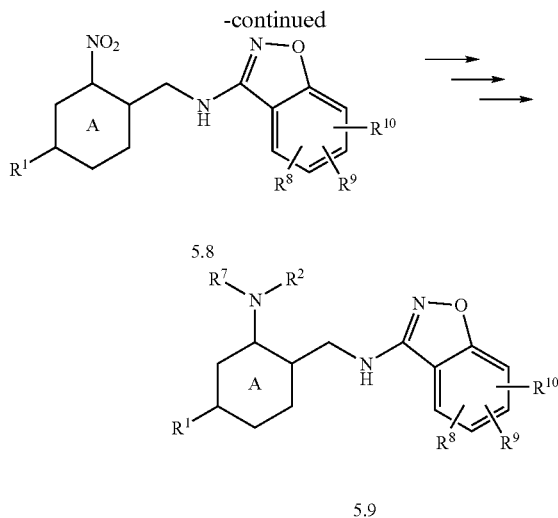

One stereoisomer of a compound of the present invention may display superior activity compared with the other. Thus, compounds of the present invention may be chiral and accordingly in various enantiomeric forms. They therefore may exist in racemic or in optically active form. When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of the present invention may also be obtained by chiral synthesis known to the person with skills in the art, e.g., synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis. An enantiomerically pure compound can be obtained with enantiomerically pure starting materials. Alternately, single stereoisomers can be obtained by chiral synthesis known to the person with skills in the art.

Other features of the invention will become apparent in the course of the following descriptions of exemplary embodiments that are given for illustration of the invention and are not intended to be limiting thereof.

EXAMPLES

Solution ratios express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923). Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "M" for molar, "mmol" for millimole or millimoles, "min" for minute or minutes, "h" for hour or hours, "rt" for room temperature, "atm" for atmosphere, "psi" for pounds per square inch, "MS" for mass spectrometry, "ESI" for electrospray ionization mass spectroscopy, "HR" for high resolution, "LC-MS" for liquid chromatography mass spectrometry, "HPLC" for high pressure liquid chromatography, "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

As used throughout the specification, the following abbreviations for chemical reagents apply:
AIBN is azo-bis-isobutyrlnitrile
Boc is tert-butyl oxycarbonyl,
BOP is benzotriazol-1-yloxy-tris(dimethylamino)phosphonium hexafluorophosphate,
Cbz is carbonylbenzyloxy,
CbzSerOtBu is (S)-2-tert-butoxycarbonylamino-3-hydroxypropionic acid tert-butyl ester,
Davis oxaziridine is 2-benzenesulfonyl-3-phenyl-oxaziridine,
DCE is 1,2-dichloroethane,
DIBAH is diisobutylaluminum hydride
DIEA is diethylpropyl amine,
DMAP is dimethylaminopyridine,
DMSO is dimethyl sulfoxide,
DMF is dimethylformamide,
DPPA is diphenylphosphoryl azide,
EDCI is 1-(3-dimethylaminopropyl)-3-ethylcarbodiimide hydrochloride,
Et is ethyl,
EtOAc is ethyl acetate,
HATU is O-(7-azabenzotriazol-1-yl)-N,N,N',N'-tetramethyluronium,
HOAc or AcOH is acetic acid,
HOAT is 1-hydroxy-7-azabenzotriazole,
LAH is lithium aluminum hydride
LDA is lithium diisopropylamide,
LiHMDS is bis(trimethylsilyl)amide,
Me is methyl,
MoOPH is oxodiperoxymolybdenum(pyridine)(hexamethylphosphoric triamide),
MsCl is methanesulfonyl chloride,
NaOAc is sodium actetate,
OAc is acetate,
Ph is phenyl,
Pr is propyl,
TBAI is tetrabutylammonium iodide,
TEA is triethylamine,
TFA is trifluoroacetic acid,
TFAA is trifluoroacetic anhydride, and
THF is tetrahydrofuran.

The following Examples have been prepared, isolated and characterized using the methods disclosed herein. The following Examples demonstrate a partial scope of the invention and are not meant to be limiting of the scope of the invention.

Example 1

N-(4-Carbamimidoyl-2-methylamino-benzyl)-3,5-dimethoxy-4-methyl-benzamide

N-Hydroxy-4-methyl-3-nitro-benzamidine (1a). TEA (25.8 mL, 185 mmol) was added to a solution of hydroxylamine hydrochloride (12.9 g, 185 mmol) in dimethylsulfoxide (62 mL). After stirring 30 min, the thick suspension was filtered through a glass fiber filter and washed several times with THF. The THF was removed in vacuo to give a solution of hydroxylamine in DMSO (~3M). 3-Nitro-p-tolunitrile (10.0 g, 61.7 mmol) was added, and the reaction mixture was heated to 60° C. for 1 h. The reaction mixture was cooled to rt and poured into water (400 mL) with stirring. The suspension was filtered, washed with water (3×), and dried in vacuo to afford compound 1a as a yellow solid (11.5 g, 95%). ESI-MS m/e 196.2 (M+1).

5-Methyl-3-(4-methyl-3-nitro-phenyl)-[1,2,4]oxadiazole (1b). Acetic anhydride (25 mL, 260 mmol) was added to a solution of compound 1a (11.5 g, 58.8 mmol) in a mixture of pyridine (50 mL, 620 mmol) and toluene (200 mL). The reaction mixture was refluxed for 22 h. After cooling to rt, a solution of concentrated HCl (75 mL) in water (200 mL) was added, and the aqueous layer was extracted with ethyl acetate. The combined organic layers were washed with saturated sodium bicarbonate solution, dried over sodium sulfate, and concentrated in vacuo. The residue was recrystallized from absolute ethanol to afford compound 1b as tan needles (9.8 g, 76%). ESI-MS m/e 220.2 (M+1).

3-(4-Bromomethyl-3-nitro-phenyl)-5-methyl-[1,2,4]oxadiazole (1c). A solution of compound 1b (21 g, 96 mmol) and N-bromosuccinimide (20.5 g, 115 mmol) in dichloromethane (500 mL) was irradiated with a sun lamp for 2 h at rt. The reaction mixture was filtered through a short column of silica gel in dichloromethane and concentrated on a rotary evaporator. The residue was recrystallized (ethyl acetate/hexane/petroleum ether) to afford compound 1c as a white solid (23.2 g, 82%). ESI-MS m/e 300.1 (M+1).

2-[4-(5-Methyl-[1,2,4]oxadiazol-3-yl)-2-nitro-benzyl]-isoindole-1,3-dione (1d). A solution of compound 1c (5.64 g, 19 mmol) and potassium pthalimide (3.9 g, 20.9 mmol) in DMF (42 mL) was heated to 40° C. for 4 h. The reaction mixture was cooled to rt and poured into water (200 mL). The solid was filtered, washed with water (3×), and dried in vacuo to give compound 1d as a white solid (6.2 g, 90%). ESI-MS m/e 365.1 (M+1).

4-(5-Methyl-[1,2,4]oxadiazol-3-yl)-2-nitro-benzylamine (1e). A solution of compound 1d (6.2 g, 17 mmol) and hydrazine hydrate (2.9 mL, 60 mmol) in absolute ethanol (165 mL) was refluxed for 3 h. The reaction mixture was cooled to rt and concentrated on a rotary evaporator. The residue was suspended in dichloromethane, filtered, and concentrated again. The filtrate was dissolved in 10% HCl (800 mL), washed 3× with dichloromethane, made basic (pH~11) with 50% NaOH, and extracted with dichloromethane (4×100 mL). The combined organic layers were washed with brine, dried ($Na_2SO_4$) and concentrated on a rotary evaporator to afford compound 1e (3.34 g, 84%) as a brown oil which solidified on standing. ESI-MS m/e 235.2 (M+1).

3,5-Dimethoxy-4-methyl-N-[4-(5-methyl-[1,2,4]oxadiazol-3-yl)-2-nitro-benzyl]-benzamide (1f). A suspension of compound 1e (3.34 g, 14.3 mmol), 3,5-dimethoxy-4-methylbenzoic acid (4.2 g, 21.4 mmol), EDCI (4.1 g, 21.4 mmol), and HOAt (190 mg, 1.4 mmol) in a mixture of dichloromethane (60 mL) and DMF (30 mL) was stirred at rt for 12 h. The reaction mixture was diluted with ethyl acetate and washed with 1 N HCl. The solid which precipitated was recovered by filtration. The ethyl acetate layer was washed with saturated $NaHCO_3$ solution and brine, dried $Na_2SO_4$, and concentrated on a rotary evaporator. The residue was recrystallized (ethyl acetate/hexane/petroleum ether) and combined with the filtered solid to afford compound 1f (5.55 g, 94%) as a cream colored solid. ESI-MS m/e 413.2 (M+1).

N-[2-Amino-4-(5-methyl-[1,2,4]oxadiazol-3-yl)-benzyl]-3,5-dimethoxy-4-methyl-benzamide (1g). A suspension of compound 1f (2.80 g, 6.81 mmol) in a mixture of ethanol (120 mL), acetic acid (6 mL) and water (24 mL) was heated to reflux. Iron powder (1.90 g, 34 mmol) was added portionwise over 45 min. The reaction mixture was cooled to rt and diluted with ethyl acetate. The ethyl acetate solution was washed with saturated $NaHCO_3$ solution, dried $Na_2SO_4$, and concentrated on a rotary evaporator to a volume of ~30 mL. The solid precipitate was recovered by filtration and washed with ethyl acetate (2×). The filtrate was passed through a short silica gel column in ethyl acetate, and concentrated on a rotary evaporator. The residue was triturated with ethyl acetate and combined with the previously filtered solid to afford compound 1g (1.83 g, 70%) as a tan solid. ESI-MS m/e 383.3 (M+1).

3,5-Dimethoxy-4-methyl-N-[4-(5-methyl-[1,2,4]oxadiazol-3-yl)-2-(2,2,2-trifluoro-acetylamino)-benzyl]-benzamide (1h). TFAA (0.48 mL, 3.4 mmol) was added dropwise to a solution of compound 1g (1.07 g, 2.8 mmol) in a mixture of pyridine (0.45 mL, 5.6 mmol) and dichloromethane (13 mL). The reaction mixture was stirred at rt for 2 h. The reaction mixture was diluted with ethyl acetate and washed with water (3×) and brine, dried $Na_2SO_4$, and concentrated on a rotary evaporator to give compound 1h (1.34 g, 100%) as a cream colored solid. ESI-MS m/e 479.2 (M+1).

3,5-Dimethoxy-4-methyl-N-{4-(5-methyl-[1,2,4]oxadiazol-3-yl)-2-[methyl-(2,2,2-trifluoro-acetyl)-amino]-benzyl}-benzamide (1i). A suspension of compound 1h (1.1 g, 2.3 mmol), methyl iodide (0.72 mL, 11.5 mmol) and potassium carbonate (1.6 g, 11.5 mmol) in acetone (14 mL) was sealed in a pressure tube and heated at 50° C. for 3 h. The reaction mixture was cooled to rt, filtered, and concentrated on a rotary evaporator to give compound 1i (1.1 g, 100%) as a light yellow solid. ESI-MS m/e 493.1 (M+1).

3,5-Dimethoxy-4-methyl-N-[2-methylamino-4-(5-methyl-[1,2,4]oxadiazol-3-yl)-benzyl]-benzamide (1j). A suspension of compound 1i (0.11 g, 0.22 mmol) and potassium carbonate (92.5 mg, 0.67 mmol) in a mixture of methanol (2.5 mL) and water (0.4 mL) was stirred at rt for 3 h. The reaction mixture was filtered and concentrated on a rotary evaporator. The residue was dissolved in ethyl acetate and washed with water and brine, dried $MgSO_4$, and concentrated to give compound 1j (30 mg, 34%). ESI-MS m/e 397.3 (M+1).

Example 1. A suspension of compound 1j (30 mg, 0.076 mmol) and 10% Pd/C (9 mg) in a mixture of methanol (1.6 mL) and acetic acid (0.4 mL) was stirred at rt under an atmosphere of hydrogen (1 atm) for 12 h. The reaction mixture was filtered and concentrated on a rotary evaporator. The residue was purified by reverse phase HPLC (C18 column, water/acetonitrile gradient containing 0.1% TFA) to give Example 1 (19 mg, 53%). ESI-MS m/e 357.3 (M+1).

Example 2

N-(2-Amino-4-carbamimidoyl-benzyl)-3,5-dimethoxy-4-methyl-benzamide

A suspension of compound 1h (50 mg, 0.10 mmol) and 10% Pd/C (20 mg) in a mixture of methanol (1.6 mL) and acetic acid (0.4 mL) was stirred at rt under an atmosphere of hydrogen (1 atm) for 12 h. The reaction mixture was filtered and concentrated on a rotary evaporator. The residue was purified by reverse phase HPLC (C18 column, water/acetonitrile gradient containing 0.1% TFA) to give Example 2 (11 mg, 23%). ESI-MS m/e 343.1 (M+1).

Example 3

N-(4-Carbamimidoyl-2-dimethylamino-benzyl)-3,5-dimethoxy-4-methyl-benzamide

A suspension of compound 1g (50 mg, 0.13 mmol), methyl iodide (0.035 mL, 0.52 mmol), and potassium carbonate (72 mg, 0.52 mmol) in DMF (1 mL) was sealed in a pressure tube and heated at 60° C. for 3 h. The reaction mixture was cooled to rt, filtered, and concentrated on a rotary evaporator. The residue was suspended in a mixture of methanol (1 mL) and acetic acid (1 mL), 10% Pd/C was added (100 mg), and the solution was hydrogenated (1 atm) for two days. The mixture was filtered, Raney Ni was added, and the mixture was again hydrogenated (1 atm). The reaction mixture was filtered and concentrated on a rotary evaporator. The residue was purified by reverse phase HPLC (C18 column, water/acetonitrile gradient containing 0.1% TFA) to give Example 3 (31 mg, 49%). ESI-MS m/e 371.4 (M+1).

Example 4

N-(4-Carbamimidoyl-2-ethylamino-benzyl)-3,5-dimethoxy-4-methyl-benzamide

A suspension of compound 1h (100 mg, 0.21 mmol), ethyl iodide (0.070 mL, 0.84 mmol) and potassium carbonate (90 mg, 0.63 mmol) in DMF (1 mL) was sealed in a pressure tube and heated at 85° C. for 16 h. The reaction mixture was cooled to rt, filtered, and concentrated on a rotary evaporator. The residue was dissolved in a mixture of methanol (7 mL) and water (1 mL) and potassium carbonate (200 mg, 1.45 mmol) was added. The reaction mixture was heated at 50° C. for 2 h. The reaction mixture was diluted with water and extracted with ethyl acetate. The organic layer was washed with brine, dried and concentrated on a rotary evaporator. The residue was dissolved in 8:2 MeOH/AcOH (7 mL) and 10% Pd/C (spatula tip) and additional AcOH (3 mL) was added. The reaction mixture was hydrogenated (1 atm) until the reaction was complete as indicated by analytical LC/MS. The reaction mixture was filtered and concentrated on a rotary evaporator. The residue was purified by reverse phase HPLC (C18 column, water/acetonitrile gradient containing 0.1% TFA) to give to give Example 4 (32 mg, 32%) as a colorless solid. ESI-MS m/e 371.3 (M+1).

Example 5

N-(4-Carbamimidoyl-2-propylamino-benzyl)-3,5-dimethoxy-4-methyl-benzamide

Compound 1h (100 mg, 0.21 mmol) was reacted with propyl iodide according to the protocol of Example 4. The trifluoroacetamide group was removed and oxadiazole converted to amidine, again following the protocols of Example 4, to give Example 5 (23 mg, 22%) as a colorless solid. ESI-MS m/e 385.3 (M+1).

Example 6

N-(2-Benzylamino-4-carbamimidoyl-benzyl)-3,5-dimethoxy-4-methyl-benzamide

Compound 1h (100 mg, 0.21 mmol) was reacted with benzyl bromide according to the protocol of Example 4. The trifluoroacetamide group was removed and oxadiazole converted to amidine, again following the protocols of Example 4, with the exception that the hydrogenation step was conducted with Raney nickel and TEA (0.175 mL, 1.26 mmol) in methanol (20 mL), to give Example 6 (20 mg, 9%) as a white solid. ESI-MS m/e 433.3 (M+1).

Example 7

N-(4-Carbamimidoyl-2-isobutylamino-benzyl)-3,5-dimethoxy-4-methyl-benzamide

N-[2-Isobutylamino-4-(5-methyl-[1,2,4]oxadiazol-3-yl)-benzyl]-3,5-dimethoxy-4-methyl-benzamide (7a). A suspension of compound 1h (200 mg, 0.42 mmol), isobutyl iodide (0.144 mL, 1.25 mmol), and potassium carbonate (173 mg, 1.25 mmol) in DMF (2 mL) was sealed in a pressure tube and heated at 85° C. for three days. Additional portions of isobutyl iodide (3 eq) were added each day. The reaction mixture was cooled to rt, diluted with ethyl acetate, washed with water and brine, dried, and concentrated on a rotary evaporator. The residue was dissolved in a mixture of methanol (10 mL) and water (1 mL), and potassium carbonate (200 mg, 1.45 mmol) was added. The reaction mixture was heated at 50° C. for 2 h. The reaction mixture was diluted with water, filtered, and concentrated on a rotary evaporator. The residue was purified by chromatography on silica gel (35% v/v ethyl acetate/hexane) to give compound 7a (100 mg, 54%) as a pale yellow solid. ESI-MS m/e 439.3 (M+1).

Example 7. Compound 7a (27 mg, 0.06 mmol) was dissolved in 8:2 MeOH/AcOH (2 mL) and 10% Pd/C (spatula tip) was added. The reaction mixture was hydrogenated (1 atm) until the reaction was complete as indicated by analytical LC/MS. The reaction mixture was filtered and concentrated on a rotary evaporator. The residue was purified by reverse phase HPLC (C18 column, water/acetonitrile gradient containing 0.1% TFA) to give to give Example 7 (32 mg, 82%) as a colorless solid. ESI-MS m/e 399.4 (M+1).

Example 8

N-(4-Carbamimidoyl-2-phenylamino-benzyl)-3,5-dimethoxy-4-methyl-benzamide 3,5-Dimethoxy-4-methyl-N-[4-(5-methyl-[1,2,4]oxadiazol-3-yl)-2-phenylamino-benzyl]-benzamide (8a). To a suspension of Pd(P(t-Bu$_3$)$_2$ (3.3 mg, 0.0065 mmol) and cetyltrimethylammonium bromide (1.2 mg, 0.0033 mmol) in toluene (2 mL) was added compound 1g (250 mg, 0.65 mmol), bromobenzene (0.072 mL, 0.68 mmol), potassium hydroxide (55 mg, 0.98 mmol), and water (0.018 mL, 0.98 mmol). The reaction mixture was heated at 90° C. for 24 h. Additional Pd(P(t-Bu$_3$)$_2$ (5 mg) and cetyltrimethyl-ammonium bromide (3 mg) was added and heating was continued for 18 h. Additional Pd(P(t-Bu$_3$)$_2$ (5 mg) was added, and the reaction was heated to 100° C. for 12 h. The reaction mixture was filtered through a column of silica gel in ethyl acetate and concentrated on a rotary evaporator. The residue was purified by chromatography on silica gel (30-40% v/v ethyl acetate/hexane) to give compound 8a (120 mg, 40%) as a colorless solid. ESI-MS m/e 459.2 (M+1).

Example 8. Compound 8a (15 mg, 0.053 mmol) was dissolved in 8:2 MeOH/AcOH (1 mL) and 10% Pd/C (spatula tip) was added. The reaction mixture was hydrogenated (1 atm) until the reaction was complete as indicated by analytical LC/MS. The reaction mixture was filtered and concentrated on a rotary evaporator. The residue was purified by reverse phase HPLC (C18 column, water/acetonitrile gradient containing 0.1% TFA) to give to give Example 8 (2 mg, 7%) as a colorless solid. ESI-MS m/e 419.4 (M+1).

Example 9

N-(4-Carbamimidoyl-2-phenethylamino-benzyl)-3, 5-dimethoxy-4-methyl-benzamide 3,5-Dimethoxy-4-methyl-N-[4-(5-methyl-[1,2,4]oxadiazol-3-yl)-2-phenethylamino-benzyl]-benzamide (9a). Acetic acid (0.040 mL, 5 eq) and sodium triacetoxyborohydride (42 mg, 0.20 mmol) were added to a suspension of compound 1g (50 mg, 0.13 mmol) and phenylacetaldehyde (0.020 mg, 2 eq) in DCE (1.5 mL). The reaction was stirred at rt for 16 h and concentrated on a rotary evaporator. The residue was purified by preparative tlc (silica gel, 1:1 ethyl acetate/hexane) to afford compound 9a. ESI-MS m/e 487.3 (M+1).

Example 9. Compound 9a was dissolved in a mixture of MeOH (3 mL) and TEA (0.040 mL, 0.29 mmol), and Raney nickel (washed with methanol) was added. The reaction mixture was hydrogenated overnight (50 psi), filtered, and concentrated on a rotary evaporator. The residue was purified by reverse phase HPLC (C18 column, water/acetonitrile gradient containing 0.1% TFA) to give to give Example 9. ESI-MS m/e 447.3 (M+1).

Example 10

N-[4-Carbamimidoyl-2-(3-phenyl-propylamino)-benzyl]-3,5-dimethoxy-4-methyl-benzamide 3,5-Dimethoxy-4-methyl-N-[4-(5-methyl-[1,2,4]oxadiazol-3-yl)-2-(3-phenyl-propylamino)-benzyl]-benzamide (10a). Compound 1g (50 mg, 0.13 mmol) was reductively aminated with hydrocinnamaldehyde (0.020 mL, 0.15 mmol) following a procedure analogous to the preparation of compound 9a to afford compound 10a. ESI-MS m/e 501.4 (M+1).

Example 10. Compound 10a was following a procedure analogous to the preparation of Example 9 to afford Example 10. ESI-MS m/e 461.3 (M+1).

Example 11

N-(4-Carbamimidoyl-2-isopropylamino-benzyl)-3,5-dimethoxy-4-methyl-benzamide

Acetic acid (0.007 mL, 0.12 mmol) and sodium triacetoxyborohydride (42 mg, 0.20 mmol) were added to a suspension of compound 1g (50 mg, 0.13 mmol) and acetone (0.010 mL, 0.14 mmol) in DCE (0.5 mL). The reaction was stirred at rt for 16 h. Trimethylorthoformate (0.5 mL) was added, and the reaction was stirred at rt for 24 h. MeOH (1 mL) was added, and the reaction was stirred for 3 h. The reaction mixture was concentrated on a rotary evaporator and the residue was purified by preparative tlc (silica gel, 9:1 chloroform/methanol). This material was dissolved in a mixture of MeOH (3 mL) and TEA (0.040 mL, 0.29 mmol), and Raney nickel (washed with methanol) was added. The reaction mixture was hydrogenated overnight (50 psi), filtered, and concentrated on a rotary evaporator. The residue was purified by reverse phase HPLC (C18 column, water/acetonitrile gradient containing 0.1% TFA) to give to give Example 11. ESI-MS m/e 385.4 (M+1).

Example 12

N-(4-Carbamimidoyl-2-cyclopentylamino-benzyl)-3, 5-dimethoxy-4-methyl-benzamide

Compound 1g (50 mg, 0.13 mmol) was reductively aminated with cyclopentanone (0.012 mL, 0.14 mmol) and subsequently hydrogenated following a procedure analogous to the preparation of compound 11a, to give example 12. ESI-MS m/e 411.4 (M+1).

Example 13

N-(4-Carbamimidoyl-2-cyclohexylamino-benzyl)-3, 5-dimethoxy-4-methyl-benzamide

Compound 1g (50 mg, 0.13 mmol) was reductively aminated with cyclohexanone (0.013 mL, 0.12 mmol) and subsequently hydrogenated following a procedure analogous to the preparation of Example 11, to give Example 13. ESI-MS m/e 425.4 (M+1).

Example 14

{5-Carbamimidoyl-2-[(3,5-dimethoxy-4-methyl-benzoylamino)-methyl]-phenylamino}-acetic acid

[2-[(3,5-Dimethoxy-4-methyl-benzoylamino)-methyl]-5-(5-methyl-[1,2,4]oxadiazol-3-yl)-phenylamino]-acetic acid benzyl ester (14a). A suspension of compound 1g (382 mg, 1.0 mmol), benzyl 2-bromoacetate (0.224 mL, 1.4 mmol), and potassium carbonate (276 mg, 2.0 mmol) in DMF (3 mL) was sealed in a pressure tube and heated at 80° C. for 5 h and at rt for two days. The reaction mixture was diluted with water, and the resulting solid precipitate was recovered by filtration and washed with MeOH and hexane to give compound 14a (252 mg, 48%) as a yellow solid. ESI-MS m/e 531.3 (M+1).

Example 14. Compound 14a (252 mg, 0.48 mmol) was dissolved in a mixture of 4:1 MeOH/AcOH (5 mL) and THF (5 mL)and 10% Pd/C (24 mg) was added. The reaction mixture was hydrogenated (50 psi) until the reaction was complete as indicated by analytical LC/MS. The reaction mixture was filtered and concentrated on a rotary evaporator. The residue was dissolved in THF containing several drops of MeOH and 10% LiOH (1 mL) was added. The reaction was stirred at rt for 3 h, concentrated on a rotary evaporator to ~1 mL volume, and acidified with 1 N HCl. The resulting precipitate was filtered, washed with water, and dried to afford Example 14 (181 mg, 95%) as a yellow solid. ESI-MS m/e 401.3 (M+1).

Example 15

3-{5-Carbamimidoyl-2-[(3,5-dimethoxy-4-methyl-benzoylamino)-methyl]-phenylamino}-propionic acid 3-[2-[(3,5-Dimethoxy-4-methyl-benzoylamino)-methyl]-5-(5-methyl-[1,2,4]oxadiazol-3-yl)-phenylamino]-propionic acid methyl ester (15a). A suspension of compound 1g (130 mg, 0.34 mmol) in methyl acrylate (1.0 mL, 11.1 mmol), and acetic acid (0.5 mL, 8.7 mmol) was sealed in a pressure tube under argon and heated at 80° C. overnight. The reaction mixture was concentrated on a rotary evaporator and the residue was purified by preparative tlc (silica gel, 40% v/v ethyl acetate/hexane) to give compound 15a (47 mg, 30%). ESI-MS m/e 469.3 (M+1).

Example 15. Compound 15a (28 mg, 0.059 mmol) was dissolved in 4:1 MeOH/AcOH and 10% Pd/C was added. The reaction mixture was hydrogenated (50 psi) until the reaction was complete as indicated by analytical LC/MS. The reaction mixture was filtered and concentrated on a rotary evaporator. The residue was dissolved in THF (1 mL) containing several drops of MeOH and 10% LiOH (1 mL) was added. The reaction was stirred at rt for 5 h, concentrated on a rotary evaporator to ~1 mL volume, and acidified with 1 N HCl. The resulting precipitate was filtered and then purified by reverse phase HPLC (C18 column, water/acetonitrile gradient containing 0.1% TFA) to give Example 15. ESI-MS m/e 415.2 (M+1).

Example 16

3-({5-Carbamimidoyl-2-[(3,5-dimethoxy-4-methyl-benzoylamino)-methyl]-phenylamino}-methyl)-benzoic acid 3-{[2-[(3,5-Dimethoxy-4-methyl-benzoylamino)-methyl]-5-(5-methyl-[1,2,4]oxadiazol-3-yl)-phenylamino]-methyl}-benzoic acid methyl ester (16a). A suspension of compound 1g (76 mg, 0.20 mmol), methyl-3-(bromomethyl)benzoate (56 mg, 0.24 mmol) and potassium carbonate (55 mg, 0.40 mmol) in DMF (1 mL) was sealed in a pressure tube and heated at 80° C. overnight. The reaction mixture was diluted with water, and the resulting solid precipitate was recovered by filtration to give compound 16a. ESI-MS m/e 531.4 (M+1).

Example 16. Compound 16a was dissolved in a mixture of MeOH (5 mL), THF (15 mL), and TEA (0.15 mL, 1.1 mmol) and Raney nickel (washed with MeOH) was added. The reaction mixture was hydrogenated (1 atm) until the reaction was complete as indicated by analytical LC/MS. The reaction mixture was filtered and concentrated on a rotary evaporator. Half of the residue was dissolved in concentrated HCl (0.5 mL). The reaction was stirred at 95° C. for two h, neutralized with 1 N NaOH, and concentrated on a rotary evaporator. The residue was purified by reverse phase HPLC (C18 column, water/acetonitrile gradient containing 0.1% TFA) to give Example 16 (1.6 mg, 3%). ESI-MS m/e 477.2 (M+1).

Example 17

4-({5-Carbamimidoyl-2-[(3,5-dimethoxy-4-methyl-benzoylamino)-methyl]-phenylamino}-methyl)-benzoic acid 4-{[2-[(3,5-Dimethoxy-4-methyl-benzoylamino)-methyl]-5-(5-methyl-[1,2,4]oxadiazol-3-yl)-phenylamino]-methyl}-benzoic acid methyl ester. (17a). Compound 1g (76 mg, 0.20 mmol) was alkylated with methyl-4-(bromomethyl)benzoate (56 mg, 0.24 mmol) following a procedure analogous to the preparation of compound 16a to give compound 17a. ESI-MS m/e 531.3 (M+1).

Example 17b. Compound 17a hydrogenated and then hydrolyzed following a procedure analogous to the preparation of Example 16 to give Example 17 (8.1 mg, 14%). ESI-MS m/e 477.2 (M+1).

Example 18

{5-Carbamimidoyl-2-[(3,5-dimethoxy-4-methyl-benzoylamino)-methyl]-phenyl}-carbamic acid methyl ester A suspension of compound 1g (100 mg, 0.26 mmol), methyl chloroformate (0.020 mL, 0.26 mmol) and potassium carbonate (72 mg, 0.52 mmol) in DCE (2 mL) was stirred at rt overnight. Additional methyl chloroformate (0.010 mL, 0.13 mmol) was added and the reaction was stirred at rt for 24 h. The reaction was concentrated on a rotary evaporator and the residue purified by silica gel chromatography (ethyl acetate). This compound was dissolved in a mixture of MeOH (2 mL) and acetic acid (0.5 mL) and 10% Pd/C (10 mg) was added. The reaction mixture was hydrogenated (50 psi) overnight, filtered, and concentrated on a rotary evaporator. The residue was purified by reverse phase HPLC (C18 column, water/acetonitrile gradient containing 0.1% TFA) to give Example 18 (9 mg, 7%). ESI-MS m/e 401.5 (M+1).

Example 19

N-[4-Carbamimidoyl-2-(3-phenyl-ureido)-benzyl]-3, 5-dimethoxy-4-methyl-benzamide

[2-[(3,5-Dimethoxy-4-methyl-benzoylamino)-methyl]-5-(5-methyl-[1,2,4]oxadiazol-3-yl)-phenyl]-carbamic acid phenyl ester (19a). A suspension of compound 1g (100 mg, 0.26 mmol), phenyl chloroformate (0.033 mL, 0.26 mmol) and potassium carbonate (72 mg, 0.52 mmol) in DCE (2 mL) was stirred at rt overnight. Additional phenyl chloroformate (0.015 mL, 0.13 mmol) was added and the reaction was stirred at rt for 24 h. The reaction was concentrated on a rotary evaporator and the residue purified by silica gel chromatography (ethyl acetate) to afford compound 19a (157 mg, 100%).

3,5-Dimethoxy-4-methyl-N-[4-(5-methyl-[1,2,4]oxadiazol-3-yl)-2-(3-phenyl-ureido)-benzyl]-benzamide (19b). A solution of compound 19a (50 mg, 0.10 mmol) and aniline (0.010 mL, 0.11 mmol) in THF was heated at 60° C. for 5 h. Additional aniline (0.010 mL, 0.11 mmol) was added and the reaction was stirred at rt overnight. Additional methyl chloroformate (0.010 mL, 0.13 mmol) was added and the reaction was stirred at rt for 24 h. The solid precipitate was recovered by filtration and washed with ethyl acetate and MeOH to give compound 19b (13 mg, 26). ESI-MS m/e 502.4 (M+1).

Example 19. A solution of compound 19b (13 mg, 0.026 mmol) was dissolved in a mixture of MeOH and TEA (0.050 mL, 0.36 mmol) and Raney nickel (washed with MeOH) was added. The reaction mixture was hydrogenated (50 psi) overnight, filtered, and concentrated on a rotary evaporator. The residue was purified by reverse phase HPLC (C18 column, water/acetonitrile gradient containing 0.1% TFA) to give Example 19 (4 mg, 27%). ESI-MS m/e 462.3 (M+1).

Example 20

N-(4-Carbamimidoyl-2-methanesulfonylamino-benzyl)-3,5-dimethoxy-4-methyl-benzamide A suspension of compound 1g (50 mg, 0.13 mmol), methanesulfonyl chloride (0.010 mL, 0.13 mmol), pyridine (0.016 mL, 0.20 mmol), and 4-dimethylaminopyridine (5 mg, 0.04 mmol) in dichloromethane was stirred at rt overnight. The reaction was concentrated on a rotary evaporator and the residue purified preparative tlc (silica gel, ethyl acetate). This compound was dissolved in a mixture of methanol (2 mL), acetic acid (1 mL), and dioxane (3 mL) and 10% Pd/C was added (spatula tip). The reaction mixture was hydrogenated (50 psi) overnight, filtered, and concentrated on a rotary evaporator. The residue was purified by reverse phase HPLC (C18 column, water/acetonitrile gradient containing 0.1% TFA) to give Example 20 (12 mg, 17%). ESI-MS m/e 421.3 (M+1).

Example 21

N-(4-Carbamimidoyl-2-phenylacetylamino-benzyl)-3,5-dimethoxy-4-methyl-benzamide

Compound 1g (50 mg, 0.13 mmol) was acylated with phenylacetyl chloride (0.017 mL, 0.13 mmol) and subsequently hydrogenated following a procedure analogous to the preparation of Example 20 to give Example 21 (13 mg, 16%). ESI-MS m/e 461.5 (M+1).

Example 22

N-[4-Carbamimidoyl-2-(phenethyl-phenylcarbamoylmethyl-amino)-benzyl]-3,5-dimethoxy-4-methyl-benzamide {[2-[(3,5-Dimethoxy-4-methyl-benzoylamino)-methyl]-5-(5-methyl-[1,2,4]oxadiazol-3-yl)-phenyl]-phenethyl-amino}-acetic acid (22a). A solution of compound 9a (45 mg, 0.092 mmol), methyl bromoacetate (0.053 mL, 0.56 mmol), and potassium carbonate (38 mg, 0.27 mmol) in DMF (1 mL) was sealed in a pressure tube and heated at 80° C. overnight and at rt for two days. Additional methyl bromoacetate (0.060 mL) and potassium carbonate (42 mg) was added and the reaction was heated at 100° C. for 5 h. The reaction mixture was filtered and concentrated on a rotary evaporator. The residue was purified by preparative tlc. This compound was dissolved in a mixture of THF (1 mL) containing several drops of MeOH and 10% LiOH (1 mL). The reaction mixture was stirred at rt for 4 h, neutralized, and concentrated on a rotary evaporator. The residue was dissolved in ethyl acetate, washed with water, dried, and concentrated to give compound 22a (31 mg, 62%). ESI-MS m/e 545.4 (M+1).

Example 22. Compound 22a (31 mg, 0.057 mmol), aniline (0.006 mL, 0.066 mmol), EDC (14 mg, 0.071 mmol), and HOAT (spatula tip) in 4:1 dichloromethane/DMF was stirred at rt for 2 days. The reaction was concentrated on a rotary evaporator. The residue was purified by preparative tlc (silica gel, 9:1 chloroform/methanol). This compound was dissolved in 4:1 methanol/acetic acid and 20% Pd(OH)$_2$/C was added. The reaction mixture was hydrogenated (1 atm) until the reaction was complete as indicated by analytical LC/MS. The reaction mixture was filtered and concentrated on a rotary evaporator to afford Example 22 (25 mg, 63%). ESI-MS m/e 580.4 (M+1).

Example 23

N-[4-Carbamimidoyl-2-(phenylcarbamoylmethyl-amino)-benzyl]-3,5-dimethoxy-4-methyl-benzamide N-[2-Benzylamino-4-(5-methyl-[1,2,4]oxadiazol-3-yl)-benzyl]-3,5-dimethoxy-4-methyl-benzamide (23a). A solution of compound 1h (200 mg, 0.42 mmol), benzyl bromide (0.100 mL, 0.84 mmol), and potassium carbonate (173 mg, 1.25 mmol) in DMF (2 mL) was sealed in a pressure tube and heated at 60° C. overnight. The reaction mixture was diluted with ethyl acetate, washed with water, dried, and concentrated on a rotary evaporator. The residue was dissolved in a mixture of MeOH (10 mL) and water (1 mL), and potassium carbonate (200 mg) was added. The reaction mixture was stirred at rt overnight. The reaction mixture was diluted with water and the precipitated solid was recovered by filtration and dried in vacuo to give compound 23a (163 mg, 82%). ESI-MS m/e 473.1 (M+1).

{Benzyl-[2-[(3,5-dimethoxy-4-methyl-benzoylamino)-methyl]-5-(5-methyl-[1,2,4]oxadiazol-3-yl)-phenyl]-amino}-acetic acid (23b). Compound 23a (163 mg, 0.35 mmol), methyl bromoacetate (0.166 mL, 1.75 mmol), and potassium carbonate (145 mg, 1.05 mmol) in DMF (2 mL) was sealed in a pressure tube and heated at 80° C. overnight. The reaction mixture was filtered through a silica gel pad in ethyl acetate and concentrated on a rotary evaporator. The residue was dissolved in a mixture of THF (3 mL) and MeOH (1 mL) and 10% LiOH (2 mL) was added. The reaction mixture was stirred overnight at rt. The reaction mixture was concentrated on a rotary evaporator, dissolved in water (50 mL), and acidified with conc. HCl. The white precipitate was filtered and dried invacuo to give compound 23b (155 mg, 83%). ESI-MS m/e 531.3 (M+1).

Example 23. Compound 23b (53 mg, 0.10 mmol), aniline (0.014 mL, 0.15 mmol), EDC (30 mg, 0.15 mmol), and HOAT (spatula tip) in 3:1 dichloromethane/DMF (2 mL) was stirred at rt overnight. The reaction was diluted with ethyl acetate, washed with water, 1 N HCl, saturated sodium bicarbonate, and brine, dried, and concentrated on a rotary evaporator. The residue was dissolved in 4:1 methanol/acetic acid (2 mL)and 10% Pd/C (spatula tip) was added. The reaction mixture was hydrogenated (1 atm) until the reaction was complete as indicated by analytical LC/MS. The reaction mixture was filtered and concentrated on a rotary evaporator. The residue was purified by reverse phase HPLC (C18 column, water/acetonitrile gradient containing 0.1% TFA) to afford Example 23 (16 mg, 27% as a colorless solid. ESI-MS m/e 476.3 (M+1).

Examples 24-41

Parallel Synthesis of a Library of 3,4-Disubstituted Benzamidines

Using a procedure analogous to that described for compound 23b, compound 1j (900 mg, 2.24 mmol) was alkylated with methyl bromoacetate and hydrolyzed to give Example 24a (885 mg, 87%) as an off-white solid. ESI-MS m/e 455.2 (M+1).

Coupling of Example 24a to Amines and Subsequent Hydrogenation to Benzamidines

Reactions were performed in parallel under the following conditions: EDC (11.5 mg, 0.06 mmol) was added to a solution of Example 24a (18.2 mg, 0.04 mmol), an amine (0.075 mmol), and HOAt (0.6 mg, 0.004 mmol) in 4:1 dichloromethane/DMF. The reactions were stirred overnight at rt. The reaction mixtures were diluted with ethyl acetate (3-4 mL), washed with 1 N HCl (1×) and saturated bicarbonate (2×), and concentrated in vacuo. The residues were dissolved in 4:1 MeOH/AcOH (3-5 mL) and 10% Pd/C (20 mg) was added. The reaction muixtures were hydrogenated overnight at rt. The reactions were filtered and concentrated under reduced pressure. The residues were purified by reverse phase LC/MS (C18 column, water/acetonitrile gradient containing 0.1% TFA) to afford Examples 24-41.

Example 42

N-(4-Carbamimidoyl-2-(2-phenoxyethylamino)benzyl)-3,5-dimethoxy-4-methylbenzamide N-(4-(5-methyl-1,2,4-oxadiazol-3-yl)-2-(2-phenoxyethylamino)benzyl)-3,5-dimethoxy-4-methylbenzamide (42a). To a solution of compound 1g (38 mg, 0.099 mmol) in DMF was added potassium carbonate (28 mg, 0.20 mmol) and 2-bromoethoxybenzene (20 mg, 0.1 mmol). The reaction mixture was heated at 80° C. in a pressure tube for seven days. During this time, two additional portions of 2-bromoethoxybenzene (20 mg each) were added. The reaction mixture was concentrated and purified by preparative thin layer chromatography in 1:1 hexane/ethyl acetate to give compound 42a. ESI-MS m/e 503.3 (M+1).

Example 42. To a solution of compound 42a in a mixture of methanol (2 mL), and TEA (0.050 mL) was added Raney nickel (freshly washed with methanol). The reaction mixture was hydrogenated (50 psi) overnight, filtered, and concentrated. The residue was purified by reverse phase HPLC (C18 column, water/acetonitrile gradient containing 0.1% TFA) to afford Example 42 (3.1 mg, 7%). ESI-MS m/e 463.3 (M+1).

Example 43

N-(4-Carbamimidoyl-2-(2-methoxyethylamino)benzyl)-3,5-dimethoxy-4-methylbenzamide Compound 1g was reacted with 1-bromo-2-methoxyethane and subsequently hydrogenated, according to the protocol described in Example 42, to give Example 43 (8.4 mg, 21%). ESI-MS m/e 401.3 (M+1).

Example 44

N-(2-(2-Aminoethylamino)-4-carbamimidoylbenzyl)-3,5-dimethoxy-4-methylbenzamide N-(2-(2-aminoethylamino)-4-(5-methyl-1,2,4-oxadiazol-3-yl)benzyl)-3,5-dimethoxy-4-methylbenzamide (44a). To a solution of compound 1g (114 mg, 0.3 mmol) and pyridine (0.049 mL, 0.60 mmol) in DMF was added 2-bromoethylamine hydrobromide (92 mg, 0.45 mmol). The reaction mixture was heated at 80° C. for three days. After two days, additional 2-bromoethylamine hydrobromide (100 mg) and tetrabutylammonium iodide (5 mg) was added. The reaction was diluted with water and made basic by addition of 1 N NaOH. The solid was recovered by filtration and washed with water. The solid was purified by preparative thin layer chromatography (9:1 chloroform/methanol) to give compound 44a (63 mg, 49%). ESI-MS m/e 426.3 (M+1).

Example 44. To a solution of compound 44a (10 mg, 0.023 mmol) in 4:1 methanol/acetic acid (1 mL) was added 10% palladium/carbon (18 mg). The reaction mixture was hydrogenated (1 atm) overnight, filtered, and concentrated. The residue was purified by reverse phase HPLC (C18 column, water/acetonitrile gradient containing 0.1% TFA) to afford Example 44 as a beige foam (6 mg, 43%). ESI-MS m/e 386.5 (M+1).

Example 45

N-(2-(2-Acetamidoethylamino)-4-carbamimidoylbenzyl)-3,5-dimethoxy-4-methylbenzamide N-(2-(2-acetamidoethylamino)-4-(5-methyl-1,2,4-oxadiazol-3-yl)benzyl)-3,5-dimethoxy-4-methylbenzamide (45a). To a solution of compound 44a (21 mg, 0.05 mmol) and pyridine (0.008 mL, 0.1 mmol) in dichloromethane (1 mL) was added acetyl chloride (0.004 mL, 0.055 mmol). The reaction mixture was stirred for 1.5 h, and additional acetyl chloride (0.004 mL) was added. After an additional 5 min, the reaction was quenched by addition of water and concentrated. The residue was purified by reverse phase HPLC (C18 column, water/acetonitrile gradient containing 0.1% TFA) to afford compound 45a (8 mg).

Example 45. To a solution of compound 45a (8 mg) in a mixture of 4:1 methanol/acetic acid (1 mL) and THF (0.5 mL) was added 10% palladium/carbon (8 mg). The reaction mixture was hydrogenated (1 atm) overnight, filtered, and concentrated. The residue was purified by reverse phase HPLC (C18 column, water/acetonitrile gradient containing 0.1% TFA) to afford Example 45 (4 mg, 17%). ESI-MS m/e 428.5 (M+1).

Example 46

N-[2-(2-Benzoylaminoethylamino)-4-carbamimidoylbenzyl]-3,5-dimethoxy-4-methylbenzamide Compound 44a was reacted with benzoyl chloride and subsequently hydrogenated, according to the protocol described in Example 45, to give Example 46 (6 mg, 25%). ESI-MS m/e 490.4 (M+1).

Example 47

N-(2-(2-Amino-2-oxoethylamino)-4-carbamimidoylbenzyl)-3,5-dimethoxy-4-methylbenzamide 2-(2-((3,5-Dimethoxy-4-methylbenzamido)methyl)-5-(5-methyl-1,2,4-oxadiazol-3-yl)phenylamino)acetic acid (47a). To a solution of compound 14a (110 mg, 0.29 mmol) in a mixture of THF (3 mL) and methanol (3 drops) was added 10% LiOH (1 mL). The reaction mixture was stirred for 5 h at rt and acidified with 1 N HCl. The resulting solid was filtered, washed with water, and dried to give compound 47a (57 mg, 52%).

Example 47. To a solution of compound 47a (19 mg, 0.043 mmol), NaHCO₃ (7.2 mg, 0.05 mmol), HOAt (0.10 mL, 0.06 mmol, 0.6 M solution in DMF), and ammonia (0.40 mL, 0.2 mmol, 0.5M solution in dioxane) in a mixture of dichloromethane (0.5 mL) and DMF (0.033 mL) was added EDCI (9 mg, 0.047 mmol). The resulting solution was stirred overnight at rt. The reaction was concentrated and the residue was triturated with water. The resulting solid was dissolved in a mixture of 4:1 methanol/acetic acid (4 mL) and THF (0.5 mL), 10% palladium/carbon was added (9 mg), and the reaction was hydrogenated (1 atm) overnight. The reaction mixture was filtered, concentrated and purified by reverse phase HPLC (C18 column, water/acetonitrile gradient containing 0.1% TFA) to afford Example 47. ESI-MS m/e 400.5 (M+1).

Example 48

N-(4-Carbamimidoyl-2-(2-(methylamino)-2-oxoethylamino)benzyl)-3,5-dimethoxy-4-methylbenzamide Using a protocol similar to that used for the conversion of compound 47a to Example 47, compound 47a was reacted with methylamine to give Example 48. ESI-MS m/e 414.5 (M+1).

Example 49

Methyl 2-(5-carbamimidoyl-2-((3,5-dimethoxy-4-methylbenzamido)methyl)phenylamino)ethylcarbamate Compound 44a was reacted with methyl chloroformate and subsequently hydrogenated, according to the protocol described in Example 45, to give Example 49 (6.6 mg, 29%). ESI-MS m/e 444.5 (M+1).

Example 50

1-(2-(5-Carbamimidoyl-2-((3,5-dimethoxy-4-methylbenzamido)methyl)phenylamino)ethyl)-3-methylurea Compound 44a was reacted with methyl isocyanate and subsequently hydrogenated, according to the protocol described in Example 45, to give example 50 (2 mg, 9%). ESI-MS m/e 443.5 (M+1).

Examples 51 and 52

N-(4-Carbamimidoyl-2-(2-hydroxyethylamino)benzyl)-3,5-dimethoxy-4-methylbenzamide and N-(2-(2-(benzyloxy)ethylamino)-4-carbamimidoylbenzyl)-3,5-dimethoxy-4-methylbenzamide N-(2-(2-(benzyloxy)ethylamino)-4-(5-methyl-1,2,4-oxadiazol-3-yl)benzyl)-3,5-dimethoxy-4-methylbenzamide (51a). Compound 1g was reacted with benzyl 2-bromoethyl ether according to the procedure described in compound 42a, to give compound 51a (79 mg, 51%). ESI-MS m/e 517.4 (M+1).

Examples 51 and 52. To a solution of compound 51a (17 mg) in a mixture of methanol (0.8 mL), TFA (0.1 mL), and THF (0.4 mL) was added 10% palladium/carbon (3 mg). The reaction mixture was hydrogenated (1 atm) for 1 h, filtered, and concentrated. The residue was dissolved in a mixture of ammonium hydroxide (0.05 mL) and methanol (0.5 mL) and heated at 50° C. for 1 h. The reaction mixture was concentrated. The residue was purified by reverse phase HPLC (C18 column, water/acetonitrile gradient containing 0.1% TFA) to afford Example 51 (5 mg), ESI-MS m/e 387.5 (M+1) and Example 52 (2 mg), ESI-MS m/e 477.4 (M+1).

Example 53

N-(4-Carbamimidoyl-2-(2-(methylsulfonamido)ethylamino)benzyl)-3,5-dimethoxy-4-methylbenzamide Compound 44a was reacted with methane sulfonyl chloride and subsequently hydrogenated, according to the procedure described in Example 45, to give Example 53 (5 mg, 22%). ESI-MS m/e 464.4 (M+1).

Example 54

N-(4-Carbamimidoyl-2-(3-(methylamino)-3-oxopropylamino)benzyl)-3,5-dimethoxy-4-methylbenzamide 3-(2-((3,5-Dimethoxy-4-methylbenzamido)methyl)-5-(5-methyl-1,2,4-oxadiazol-3-yl)phenylamino)propanoic acid (54a). To a solution of compound 15a (89 mg, 0.19 mmol) in THF (1 mL) was added 10% LiOH (1 mL). The reaction mixture was stirred for 1 h at rt, and then acidified with 1 N HCl. This mixture was extracted with dichloromethane. The combined organic phases were dried and concentrated to give compound 54a (80 mg, 93%) as a beige foam. ESI-MS m/e 455.3 (M+1).

Example 54. To a solution of compound 54a (16 mg, 0.036 mmol), TEA (0.010 mL), HOAt (0.072 mL, 0.04 mmol, 0.6 M solution in DMF), and methylamine (0.108 mL, 0.22 mmol, 2 M solution in THF) in dichloromethane (0.4 mL) was added EDCI (8 mg, 0.042 mmol). The resulting solution was stirred overnight at rt. The reaction was concentrated and the residue was triturated with water. This material was dissolved in a mixture of dichloromethane (0.8 mL) and TFA (0.1 mL), 10% palladium/carbon was added, and the reaction was hydrogenated (1 atm) 1 h at rt. The reaction mixture was filtered and concentrated. The residue was dissolved in a mixture of methanol (0.5 mL) and ammonium hydroxide (0.050 mL) and heated at 50° C. for 1 h. The reaction mixture was concentrated and the residue was purified by reverse phase HPLC (C18 column, water/acetonitrile gradient containing 0.1% TFA) to afford Example 54 (7.5 mg, 49%). ESI-MS m/e 428.5 (M+1).

Example 55

N-(4-Carbamimidoyl-2-(3-oxo-3-(phenylamino)propylamino)benzyl)-3,5-dimethoxy-4-methylbenzamide Compound 54a was reacted with aniline and subsequently hydrogenated, according to the procedure described in Example 54, to give Example 55 (7.5 mg, 39%). ESI-MS m/e 490.5 (M+1).

Example 56

3-(5-Carbamimidoyl-2-((3,5-dimethoxy-4-methylbenzamido)methyl)phenylamino)benzoic acid Compound 1g was reacted with methyl-3-bromobenzoate and subsequently hydrogenated and the methyl ester hydrolyzed, according to the procedure described in Example 8, to give Example 56 (6 mg). ESI-MS m/e 463.4 (M+1).

Example 57

4-(5-Carbamimidoyl-2-((3,5-dimethoxy-4-methylbenzamido)methyl)phenylamino)benzoic acid Compound 1g was reacted with methyl-4-bromobenzoate and subsequently hydrogenated and the methyl ester hydrolyzed, according to the procedure described in Example 8, to give Example 57 as a yellow solid (14 mg, 34%). ESI-MS m/e 463.4 (M+1).

Example 58

2-(5-Carbamimidoyl-2-((3-(trifluoromethoxy)benzamido)methyl)phenylamino)acetic acid tert-Butyl 4-(5-methyl-1,2,4-oxadiazol-3-yl)-2-nitrobenzylcarbamate (58a). To a solution of compound 1e (0.54 g, 2.31 mmol) in acetonitrile (25 mL) at 0° C. was added di-tert-butyl dicarbonate (0.554 g, 2.53 mmol). After 1 h, the reaction mixture was concentrated. The residue was dissolved in ethyl acetate and washed with saturated sodium bicarbonate solution and brine, dried, and concentrated to give compound 58a (0.80 g, 100%).

tert-Butyl 2-amino-4-(5-methyl-1,2,4-oxadiazol-3-yl) benzylcarbamate (58b). To a solution of compound 58a (0.752 g, 2.25 mmol) in ethanol (12 mL) was added tin(II) chloride (1.62 g, 8.5 mmol). The reaction mixture was heated at 70° C. for 50 min, then cooled to rt. Saturated sodium bicarbonate solution was added. The resulting emulsion was filtered through Celite®, followed by ethyl acetate washes. The combined organic layers were washed with brine, dried, and concentrated to give compound 58b (0.57 g, 83%) as a yellow solid. ESI-MS m/e 305.5 (M+1).

Benzyl 2-(2-((tert-butoxycarbonyl)methyl)-5-(5-methyl-1,2,4-oxadiazol-3-yl)phenylamino)acetate (58c). To a solution of compound 58b (0.57 g, 1.88 mmol) and potassium carbonate (0.519 g, 3.76 mmol) in DMF (6 mL) in a pressure tube was added benzyl-2-bromoacetate (0.447 mL, 2.8 mmol). The reaction mixture was heated at 80° C. overnight, then cooled to rt. Water was added, and the mixture was extracted with ethyl acetate (3×). The combined organics were washed with water and brine, dried, and concentrated. The residue was purified by silica gel chromatography using a gradient from 10 to 30% ethyl acetate in hexanes to give compound 58c (0.68 g, 80%) as a clear oil. ESI-MS m/e 453.5 (M+1).

Benzyl 2-(2-(aminomethyl)-5-(5-methyl-1,2,4-oxadiazol-3-yl)phenylamino)acetate hydrochloride (58d). 2 N hydrogen chloride in ether (10 mL) was added to compound 58c (0.68 g, 1.5 mmol). The reaction mixture was stirred at rt for 4 h and then concentrated to give compound 58d (0.55 g, 94%). ESI-MS m/e 353.5 (M+1).

Benzyl 2-(5-(5-methyl-1,2,4-oxadiazol-3-yl)-2-((3-(trifluoromethoxy)benzamido)methyl)phenylamino)acetate (58e). To a solution of compound 58d (50 mg, 0.13 mmol), TEA (0.027 mL), HOAt (1.8 mg) and EDCI (37 mg, 0.19 mmol) in a mixture of dichloromethane (0.8 mL) and DMF (0.3 mL) was added 3-trifluoromethoxybenzoic acid (27 mg, 0.13 mmol). The resulting solution was stirred overnight at rt, and then concentrated. The residue was triturated with water, and then purified by reverse phase HPLC (C18 column, water/acetonitrile gradient containing 0.1% TFA) to afford compound 58e (30 mg, 43%). ESI-MS m/e 541.4 (M+1).

Example 58. To a solution of compound 58e (30 mg, 0.056 mmol) in a mixture of 4:1 methanol/acetic acid (2 mL) and THF (2 mL) was added 10% palladium/carbon (12 mg). The reaction mixture was hydrogenated (50 psi) overnight, filtered, and concentrated. The residue was purified by reverse phase HPLC (C18 column, water/acetonitrile gradient containing 0.1% TFA) to afford example 58 (21 mg, 72%). ESI-MS m/e 411.4 (M+1).

Example 59

2-(5-Carbamimidoyl-2-((3-ethylbenzamido)methyl) phenylamino)acetic acid

Compound 58d was reacted with 3-ethylbenzoic acid and subsequently hydrogenated according to the procedure described in Example 58, to give Example 59. ESI-MS m/e 355.5 (M+1).

Example 60

2-(5-Carbamimidoyl-2-((3-methylbenzamido)methyl)phenylamino)acetic acid

Compound 58d was reacted with 3-methylbenzoic acid and subsequently hydrogenated according to the procedure described in Example 58, to give Example 60. ESI-MS m/e 341.5 (M+1).

Example 61

2-(5-Carbamimidoyl-2-((3,4-dimethylbenzamido) methyl)phenylamino)acetic acid Compound 58d was reacted with 3,4-dimethylbenzoic acid and subsequently hydrogenated according to the the procedure described in Example 58, to give Example 61. ESI-MS m/e 355.5 (M+1).

Example 62

2-(2-(Benzamidomethyl)-5-carbamimidoylphenylamino)acetic acid

Compound 58d was reacted with benzoic acid and subsequently hydrogenated according to the the procedure described in Example 58, to give Example 62. ESI-MS m/e 327.5 (M+1).

Example 63

2-(5-Carbamimidoyl-2-((3-(trifluoromethyl)benzamido)methyl)phenylamino)acetic acid Compound 58d was reacted with 3-trifluoromethylbenzoic acid and subsequently hydrogenated according to the procedure described in Example 58, to give Example 63. ESI-MS m/e 395.4 (M+1).

Example 64

2-(5-Carbamimidoyl-2-((3-chlorobenzamido)methyl) phenylamino)acetic acid

Compound 58d was reacted with 3-chlorobenzoic acid and subsequently hydrogenated according to the procedure described in Example 58, with the exception that Raney nickel and TEA in methanol was used for the hydrogenation step, to give Example 64. ESI-MS m/e 361.5 (M+1).

Example 65

N-(4-(Aminomethyl)-2-(methylamino)benzyl)-3,5-dimethoxy-4-methylbenzamide 4-(Bromomethyl)-3-nitrobenzonitrile (65a). A solution of 4-methyl-3-nitro-benzonitrile (3.0 g, 18.5 mmol), N-bromosuccinimide (4.12 g), and benzoyl peroxide (0.224 g) in carbon tetrachloride was refluxed overnight. The reaction mixture was diluted with dichloromethane and washed with sodium bicarbonate solution and brine, dried, and concentrated. The residue was purified by silica gel chromatography in 10% ethyl acetate hexanes to give compound 65a (2.0 g, 45%).

tert-Butyl 4-(bromomethyl)-3-nitrobenzylcarbamate (65b). To a refluxing solution of compound 65a (1.40 g, 5.8 mmol) in THF was added borane dimethylsulfide complex (3.78 mL, 2M solution in THF). The reaction mixture was refluxed for 1.5 h, and then concentrated to a volume of ~20 mL. 1 M HCl in methanol (18 mL) was added. The reaction mixture was refluxed for 2 h, and then concentrated. The residue was dissolved in THF (25 mL), and di-tert-butyl dicarbonate (5.8 mL, 5.8 mmol, 1.0 M in THF) and TEA (1.2 mL) were added. The reaction mixture was stirred at rt for 3 h. The reaction mixture was concentrated, diluted with ethyl acetate, washed with saturated sodium bircarbonate and brine, dried, and concentrated. The residue was purified by silica gel chromatography in 20% ethyl acetate in hexanes to give compound 65b (1.1 g, 55%).

tert-Butyl 4-(aminomethyl)-3-nitrobenzylcarbamate (65c). A mixture of compound 65b (1.08 g, 3.11 mmol) and potassium phthalimide (0.634 g) in DMF (10 mL) was stirred at rt overnight. Additional potassium phthalimide (0.063 g) was added and stirring was continued for 4 h. The reaction was diluted with ethyl acetate, washed with water and brine, dried, and concentrated. The residue was dissolved in ethanol (20 mL) and hydrazine (0.34 mL) was added. The reaction mixture was refluxed for 1 h, and then cooled and filtered. The filtrate was concentrated to give compound 65c (1.04 g). ESI-MS m/e 282 (M+1).

tert-Butyl 4-((3,5-dimethoxy-4-methylbenzamido)methyl)-3-nitrobenzylcarbamate (65d). DMF (2 drops) and thionyl chloride (0.080 mL, 1.1 mmol) were sequentially added to a suspension of 3,5-dimethoxy-4-methyl benzoic acid (0.0995 g, 0.507 mmol) in benzene (2 mL). The reaction mixture was heated at reflux for 2 h, and then concentrated. The residue was dissolved in dichloromethane (1 mL) and then added dropwise to a solution of compound 65c (0.144 g, 0.512 mmol) and TEA (0.2 mL, 1.4 mmol) in dichloromethane (1 mL). The reaction mixture was stirred overnight at rt. The mixture was diluted with ethyl acetate and washed with 0.1 N HCl (2×) and saturated sodium bicarbonate solution, dried, and concentrated to give compound 65d (0.233 g, 100%) as a yellow solid ESI-MS m/e 460.4 (M+1).

tert-Butyl 3-amino-4-((3,5-dimethoxy-4-methylbenzamido)methyl)benzylcarbamate (65e). To a solution of compound 65d (0.170 g, 0.37 mmol) in ethanol (3 mL) was added 10% palladium/carbon (30 mg). The reaction mixture was hydrogenated (1 atm) overnight. The solution was filtered and the filtrate was concentrated to give compound 65e (0.159 g, 100%) as a brown oily solid. ESI-MS m/e 430.5 (M+1).

tert-Butyl 4-((3,5-dimethoxy-4-methylbenzamido)methyl)-3-(2,2,2-trifluoroacetamido)benzylcarbamate (65f). To a solution of 65e (0.151 g, 0.351 mmol) and pyridine (0.057 mL, 0.705 mmol) in dichloromethane (4 mL) was added dropwise TFA (0.054 mL, 0.382 mmol) at rt. The reaction was stirred overnight. Additional portions of TFAA were added until no starting material was observed by thin layer chromatography. The reaction mixture was diluted with dichloromethane, washed with saturated bicarbonate solution (2×), dried, and concentrated. The residue was purified by chromatography on silica gel in 40% ethyl acetate in hexanes to afford compound 65f (0.147, 79%) as a colorless oil. ESI-MS m/e 548.4 (M+23).

Example 65. A pressure tube was charged with compound 65f (0.0573 g, 0.109 mmol), acetone (1 mL), methyl iodide (0.020 mL, 0.32 mmol), and potassium carbonate (0.033 g, 0.24 mmol). The reaction mixture was heated at 50° C. for 3 h. The mixture was diluted with ethyl acetate, washed with water (2×), dried and concentrated. The residue was dissolved in a mixture of methanol (2.5 mL) and water (0.5 mL) and potassium carbonate (0.052 g, 0.38 mmol) was added. The reaction was stirred overnight at rt. THF (1 mL) and additional potassium carbonate (0.066 g, 0.48 mmol) was added and the reaction mixture was stirred for 5 h. The mixture was diluted with ethyl acetate, washed with water (2×), dried and concentrated. The residue was dissolved in 1:1 TFA/dichloromethane (several mL) and stirred at rt for 1 h. The mixture was concentrated, and the residue was purified by reverse phase HPLC (C18 column, water/acetonitrile gradient containing 0.1% TFA) to afford example 65 (45.7 mg, 92%). ESI-MS m/e 344 (M+1).

Example 66

2-(5-Carbamimidoyl-2-((3-methoxybenzamido)methyl)phenylamino)acetic acid

Compound 58d was reacted with m-anisic acid and subsequently hydrogenated according to the procedure described in Example 58, to give example 66. ESI-MS m/e 357.5 (M+1).

Example 67

2-(5-Carbamimidoyl-2-((3-hydroxybenzamido)methyl)phenylamino)acetic acid

Compound 58d was reacted with 3-hydroxybenzoic acid and subsequently hydrogenated according to the procedure described in Example 58, to give example 67. ESI-MS m/e 343.5 (M+1).

Example 68

2-(5-Carbamimidoyl-2-((3-methoxy-4-methylbenzamido)methyl)phenylamino)acetic acid Compound 58d was reacted with 3-methoxy-4-methylbenzoic acid and subsequently hydrogenated according to the procedure described in Example 58, to give example 68. ESI-MS m/e 371.5 (M+1).

Example 69

2-(5-(Aminomethyl)-2-((3,5-dimethoxy-4-methylbenzamido)methyl)phenylamino)acetic acid Compound 65f was reacted with tert-butyl bromoacetate and deprotected according to the the procedure described in Example 65, to give Example 69. ESI-MS m/e 388.5 (M+1).

Various analogs synthesized using Schemes and methods disclosed herein are listed in the Table 1 below.

TABLE 1

| # | $R^2$ | $R^7$ | MS (M + 1) |
|---|---|---|---|
| 1 | Me | H | 357.3 |
| 2 | H | H | 343.1 |
| 3 | Me | Me | 371.4 |
| 4 | Et | H | 371.3 |
| 5 | Pr | H | 371.3 |
| 6 | benzyl | H | 433.3 |
| 7 | i-Bu | H | 399.4 |
| 8 | phenyl | H | 419.4 |
| 9 | phenethyl | H | 447.3 |
| 10 | phenylpropyl | H | 461.3 |
| 11 | i-Pr | H | 385.4 |
| 12 | cyclopentyl | H | 411.4 |
| 13 | cyclohexyl | H | 425.4 |
| 14 | —$CH_2CO_2H$ | H | 401.3 |
| 15 | —$(CH_2)_2CO_2H$ | H | 415.2 |
| 16 | 3-$CO_2$H-benzyl | H | 477.2 |
| 17 | 4-$CO_2$H-benzyl | H | 477.2 |
| 18 | —$CO_2$Me | H | 401.5 |
| 19 | —CONHPh | H | 462.3 |
| 20 | —$SO_2$Me | H | 421.3 |
| 21 | —CO-benzyl | H | 461.5 |
| 22 | —$CH_2$CONHPh | phenethyl | 580.4 |
| 23 | —$CH_2$CONHPh | H | 476.3 |
| 24 | —$CH_2$CON(Me)HPh | Me | 504.4 |
| 25 | —$CH_2$—CONH(2-pyridyl) | Me | 491.4 |
| 26 | —$CH_2$—CONH(3-pyridyl) | Me | 491.4 |
| 27 | —$CH_2$—CONH(4-pyridyl) | Me | 492.4 |
| 28 | —$CH_2$CONH(2-Me—Ph) | Me | 504.4 |
| 29 | —$CH_2$CONH(3-Me—Ph) | Me | 504.4 |
| 30 | —$CH_2$CONH(4-Me—Ph) | Me | 504.4 |
| 31 | —$CH_2$CONH(2-F—Ph) | Me | 508.4 |
| 32 | —$CH_2$CONH(3-F—Ph) | Me | 508.4 |
| 33 | —$CH_2$CONH(4-F—Ph) | Me | 508.4 |
| 34 | —$CH_2$CONH(2-OMe—Ph) | Me | 520.5 |
| 35 | —$CH_2$CONH(3-OMe—Ph) | Me | 520.5 |
| 36 | —$CH_2$CONH(4-OMe—Ph) | Me | 520.5 |
| 37 | —$CH_2$CONH(2-thiazolyl) | Me | 497.3 |
| 38 | —$CH_2$CONH(2-Me-2H-3-pyrazolyl) | Me | 494.4 |
| 39 | —$CH_2$CONH(cyclohexyl) | Me | 496.5 |
| 40 | —$CH_2$CONH(cyclopentyl) | Me | 482.4 |
| 41 | —$CH_2$CON($CH_3$)(cyclohexyl) | Me | 510.5 |
| 42 | —$CH_2CH_2$OPh | H | 463.3 |
| 43 | —$CH_2CH_2$OMe | H | 401.3 |
| 44 | —$CH_2CH_2NH_2$ | H | 386.5 |
| 45 | —$CH_2CH_2$NHCOMe | H | 428.5 |
| 46 | —$CH_2CH_2$NHCOPh | H | 490.4 |
| 47 | —$CH_2CONH_2$ | H | 400.5 |
| 48 | —$CH_2$CONHMe | H | 414.5 |
| 49 | —$CH_2CH_2NHCO_2$Me | H | 444.5 |
| 50 | —$CH_2CH_2$NHCONHMe | H | 443.5 |
| 51 | —$CH_2CH_2$OH | H | 387.5 |
| 52 | —$CH_2CH_2$O(benzyl) | H | 477.4 |
| 53 | —$CH_2CH_2NHSO_2$Me | H | 464.4 |
| 54 | —$CH_2CH_2$CONHMe | H | 428.5 |
| 55 | —$CH_2CH_2$CONHPh | H | 490.5 |
| 56 | 3-$CO_2$H—Ph | H | 463.4 |
| 57 | 4-$CO_2$H—Ph | H | 463.4 |

TABLE 2

| # | $R^1$ | $R^2$ | $R^8$ | MS (M + 1) |
|---|---|---|---|---|
| 58 | —C(=NH)$NH_2$ | —$CH_2$—$CO_2$H | 3-$OCF_3$—Ph | 411.4 |
| 59 | —C(=NH)$NH_2$ | —$CH_2$—$CO_2$H | 3-Et—Ph | 355.5 |
| 60 | —C(=NH)$NH_2$ | —$CH_2$—$CO_2$H | 3-Me—Ph | 341.5 |
| 61 | —C(=NH)$NH_2$ | —$CH_2$—$CO_2$H | 3,4-diMe—Ph | 355.5 |
| 62 | —C(=NH)$NH_2$ | —$CH_2$—$CO_2$H | Ph | 327.5 |
| 63 | —C(=NH)$NH_2$ | —$CH_2$—$CO_2$H | 3-$CF_3$—Ph | 395.4 |
| 64 | —C(=NH)$NH_2$ | —$CH_2$—$CO_2$H | 3-Cl—Ph | 361.5 |
| 65 | —$CH_2NH_2$ | Me | 4-Me-3,5-di(OMe)—Ph | 344 |
| 66 | —C(=NH)$NH_2$ | —$CH_2$—$CO_2$H | 3-OMe—Ph | 357.5 |
| 67 | —C(=NH)$NH_2$ | —$CH_2$—$CO_2$H | 3-OH—Ph | 343.5 |
| 68 | —C(=NH)$NH_2$ | —$CH_2$—$CO_2$H | 3-OMe-4-Me—Ph | 371.5 |
| 69 | —$CH_2NH_2$ | —$CH_2$—$CO_2$H | 4-Me-3,5-di(OMe)—Ph | 388.5 |

UTILITY

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders" as used herein includes arterial or venous cardiovascular or cerebovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade, more specifically, inhibition of the coagulation factors: factor VIIa, factor IXa, factor Xa, factor XIa or thrombin.

The effectiveness of compounds of the present invention as inhibitors of the coagulation factors VIIa, IXa, Xa, XIa, or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of pNA, which was monitored spectrophotometrically by measuring the increase in absorbance at 405 nM, or the release of AMC (amino methylcoumarin, which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. Compounds tested in the assay for Factor VIIa are considered to be active if they exhibit a $K_i$ of equal to or less than 25 µM. Preferred compounds of the present invention have $K_i$'s of equal to or less than 1 µM. More preferred compounds of the present invention have $K_i$'s of equal to or less than 0.1 µM. Even more preferred compounds of the present invention have $K_i$'s of equal to or less than 0.01 µM. Compounds of the present invention have demonstrated $K_i$ values of equal to or less than 25 µM in the assay for Factor VIIa, thereby confirming the utility of the compounds of the present invention as effective inhibitors of coagulation factor VIIa.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M. Compounds tested in the Factor IXa assay are considered to be active if they exhibit a $K_i$ of equal to or less than 25 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu(gamma-OMe, 50%)-Gly-Arg-pNA; Chromogenix) at a concentration of 0.0002-0.0003 M. Compounds tested in the Factor Xa assay are considered to be active if they exhibit a $K_i$ of equal to or less than 25 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. Compounds tested in the Factor XIa assay are considered to be active if they exhibit a $K_i$ of equal to or less than 25 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. Compounds tested in the thrombin assay are considered to be active if they exhibit a $K_i$ of equal to or less than 25 µM.

Compounds of the present invention have demonstrated $K_i$ values of equal to or less than 25 µM in at least one of the above assays, thereby confirming the utility of the compounds of the present invention as effective inhibitors of the coagulation cascade and useful as anticoagulants for the prevention or treatment of thromboembolic disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_i$ values:

$(v_o-v_s)/v_s = I/(K_i(1+S/K_m))$ for a competitive inhibitor with one binding site; or $v_s/v_o = A + ((B-A)/1+((IC_{50}/(I)^n)))$ and $K_i = IC_{50}/(1+S/K_m)$ for a competitive inhibitor where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-Venous Shunt Thrombosis Model:

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of the present invention may also be useful as inhibitors of additional serine proteases, notably human thrombin, plasma kallikrein and plasmin. Because of their inhibitory action, these compounds are indicated for use in the prevention or treatment of physiological reactions, including blood coagulation, fibrinolysis, blood pressure regulation, inflammation, and wound healing catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention, when administered alone or in combination with an additional therapeutic agent to a mammal, is effective to treat (i.e. prevent, inhibit or ameliorate) the thromboembolic disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin, heparin (either unfractionated heparin or any commercially available low molecular weight heparin, for example LOVANOX™), synthetic pentasaccharide, direct acting thrombin inhibitors including hirudin and argatroban, as well as other factor VIIa, VIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K⁺ channel openers such as $I_{Ach}$ inhibitors, and $I_{Kur}$ inhibitors (e.g., compounds such as those disclosed in WO01/40231).

The term antihypertensive agents, as used herein, include, alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril), angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat gemopatrilat, nitrates) and β-blockers (for example propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriarmycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, factor VIIa, IXa, Xa and/or XIa. Such compounds may be provided in a commercial kit, for example, for use in pharmaceutical research involving thrombin, factor VIIa, IXa, Xa and/or XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, factor VIIa, IXa, Xa, and/or XIa. For example, the presence of thrombin, factor VIIa, IXa, Xa and/or XIa in an unknown sample could be determined by addition of the relevant chromogenic substrate, for example, S2288 for factor VIIa, to a series of solutions containing test sample and optionally one of the compounds of the present invention. If production of pNA is observed in the solutions containing test sample, but not in the presence of a compound of the present invention, then one would conclude factor VIIa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

DOSAGE AND FORMULATION

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The invention claimed is:

1. A compound of Formula (I):

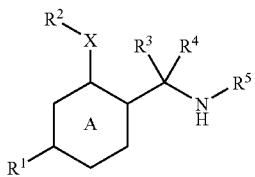

(I)

or a stereoisomer or a pharmaceutically acceptable salt or solvate form thereof, wherein:

ring A is phenyl;
wherein the phenyl is further substituted with 0-2 $R^6$;
X is $NR^7$;
$R^1$ is $-CH_2NR^{1a}R^{1b}$ or $-C(=NR^{1c})NHR^{1d}$;
$R^{1a}$ is, independently at each occurrence, H or $C_1$-$C_3$ alkyl;
$R^{1b}$ is, independently at each occurrence, H or $C_1$-$C_3$ alkyl;
$R^{1c}$ is, independently at each occurrence, H or $C_1$-$C_4$ alkyl;
$R^{1d}$ is, independently at each occurrence, H or $C_1$-$C_4$ alkyl;
$R^2$ is Y-Z-$R^{2a}$;
Y is a bond, $C_1$-$C_8$ alkylene substituted with 0-3 $R^{2d}$, $C_2$-$C_8$ alkenylene substituted with 0-3 $R^{2d}$, or $C_2$-$C_8$ alkynylene substituted with 0-3 $R^{2d}$;
Z is absent, $-O-$, $-NR^{2b}-$, $-NR^{2b}C(O)-$, $-NR^{2b}C(O)O-$, $-NR^{2b}C(O)NR^{2b}-$, $-NR^{2b}S(O)_2-$, $-S(O)_2-$, $-C(O)O-$, $-C(O)NR^{2b}-$, or $-C(O)-$;
provided that X—Y-Z do not combine to form a N—O bond;
$R^{2a}$ is, independently at each occurrence, H, $R^{2c}$, $C_1$-$C_6$ alkyl substituted with 1 $R^{2c}$, or $C_1$-$C_8$ alkyl substituted with 0-3 $R^{2d}$;
$R^{2b}$ is, independently at each occurrence, H, $C_1$-$C_3$ alkyl or phenyl;
$R^{2c}$ is, independently at each occurrence, $C_3$-$C_6$ monocycloalkyl substituted with 0-3 $R^{2e}$, phenyl substituted with 0-3 $R^{2e}$, or 5-6 membered unsaturated, partially unsaturated or saturated heterocycle consisting of carbon atoms and 1-4 heteroatoms independently chosen from O, N, and S, and substituted with 0-3 $R^{2e}$;

$R^{2d}$ is, independently at each occurrence, halogen, $-CF_3$, $C_1$-$C_6$ alkyl, or $C_1$-$C_6$ alkoxy;
$R^{2e}$ is, independently at each occurrence, halogen, $-CF_3$, $C_1$-$C_6$ alkyl, $C_1$-$C_6$ alkoxy, $-CN$, $-NO_2$, $=O$, $-OR^{2f}$, $-OC(O)R^{2f}$, $-OC(O)OR^{2f}$, $-OC(O)NR^{2b}R^{2f}$, $-NR^{2b}R^{2f}$, $-NR^{2b}C(O)R^{2f}$, $-NR^{2b}C(O)OR^{2f}$, $-NR^{2b}C(O)NR^{2b}R^{2f}$, $-NR^{2b}S(O)_2R^{2f}$, $-NR^{2b}S(O)_2NR^{2b}R^{2f}$, $-C(O)R^{2f}$, $-C(O)OR^{2f}$, $-C(O)NR^{2b}R^{2f}$, $-C(O)NHS(O)_2R^{2f}$, $-S(O)_2NHC(O)R^{2f}$, or $-C(O)NHC(O)R^{2f}$;
$R^{2f}$ is, independently at each ocurrence, H, $C_1$-$C_6$ alkyl, phenyl, benzyl, or $CF_3$;
$R^3$ is H, F, or $CH_3$;
$R^4$ is H, F, or $CH_3$;
alternatively, $R^3$ and $R^4$ are taken together to form $-CH_2CH_2-$, $-CH_2CH_2CH_2-$, $-CH_2CH_2CH_2CH_2-$, or $-CH_2CH_2CH_2CH_2CH_2-$;
$R^5$ is:

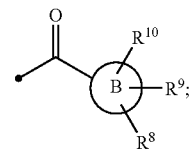

ring B is $C_6$-$C_{10}$ aryl;
$R^6$ is, independently at each ocurrence, H, $C_1$-$C_3$ alkyl, halogen, $-CF_3$, $-OH$, $C_1$-$C_3$ alkoxy, or $-OCF_3$;
$R^7$ is H, $C_1$-$C_6$ alkyl, phenyl, benzyl, or phenethyl;
$R^8$ is, independently at each ocurrence, H, halogen, $-CF_3$, $C_1$-$C_6$ alkyl, or $C_1$-$C_6$ alkoxy;
$R^9$ is, independently at each ocurrence, H, halogen, $-CF_3$, $C_1$-$C_6$ alkyl, or $C_1$-$C_6$ alkoxy; and
$R^{10}$ is, independently at each ocurrence, H, halogen, $-CF_3$, $C_1$-$C_6$ alkyl, or $C_1$-$C_6$ alkoxy;
provided that:
when B is phenyl, $R^2$ is other than H or $C_1$-$C_3$ alkyl.

2. A compound according to claim 1, wherein:
each $R^{1c}$ is, independently at each occurrence, H; and
each $R^{1d}$ is, independently at each occurrence, H.

3. A compound according to claim 2, wherein:
ring A is phenyl substituted with 0-2 $R^6$;
X is $NR^7$;
$R^3$ is H, F, or $CH_3$;
$R^4$ is H, F, or $CH_3$;
$R^5$ is:

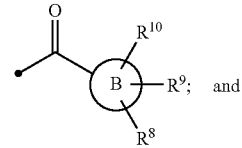

and ring B is phenyl;
provided that when when A is phenyl and B is phenyl, then $R^2$ is other than H or $C_1$-$C_3$ alkyl.

4. A compound according to claim 3, wherein:
$R^2$ is $R^{2c}$, $C_1$-$C_6$ alkyl substituted with 0-2 $R^{2d}$, $-(CH_2)_{0-3}C(=O)R^{2a}$, $-(CH_2)_{0-3}C(=O)OR^{2a}$, $-(CH_2)_{0-3}C(=O)NR^{2b}R^{2a}$, $-(CH_2)_{0-3}SO_2R^{2a}$, $-(CH_2)_{0-3}NR^{2b}C(O)R^{2a}$, or $-(CH_2)_{0-3}NR^{2b}S(O)_2R^{2a}$.

5. A compound according to claim 4, wherein:
ring A is phenyl substituted with 0-1 $R^6$;
$R^1$ is —$CH_2NH_2$, —$CH_2NH(C_1$-$C_4$ alkyl), —$CH_2N(C_1$-$C_4$ alkyl)$_2$, or —$C(=NH)NH_2$;
X is $NR^7$;
$R^3$ is H or $CH_3$;
$R^4$ is H, or $CH_3$;
$R^5$ is

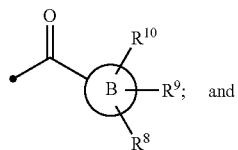

and;
$R^7$ is H, $C_1$-$C_4$ alkyl, benzyl, or phenethyl.

6. A compound according to claim 5, wherein:
$R^2$ is $C_4$-$C_6$ alkyl, $C_1$-$C_6$ alkyl substituted with 1 $R^{2d}$, $C_3$-$C_8$ cycloalkyl, phenyl-$(CH_2)_{0-3}$— substituted with 0-2 $R^{2e}$, —$(CH_2)_{0-3}C(O)R^{2a}$, —$(CH_2)_{0-3}C(O)OR^{2a}$, —$(CH_2)_{0-3}C(O)NR^{2b}R^{2a}$, —$SO_2R^{2a}$, —$(CH_2)_{0-3}NR^{2b}C(O)R^{2a}$, or —$(CH_2)_{0-3}NR^{2b}S(O)_2R^{2a}$; and
$R^{2a}$ is, independently at each occurrence, H, $C_1$-$C_4$ alkyl substituted with 0-1 $R^{2d}$, $C_3$-$C_6$ cycloalkyl substituted with 0-1 $R^{2e}$, phenyl substituted with 0-1 $R^{2e}$, benzyl substituted with 0-1 $R^{2e}$, or 5-6 membered heteroaryl substituted with 0-1 $R^{2e}$.

7. A compound according to claim 6, wherein:
ring A is phenyl;
X is NH;
$R^1$ is —$C(=NH)NH_2$ or —$CH_2NH_2$;
$R^3$ is H;
$R^4$ is H; and
$R^5$ is

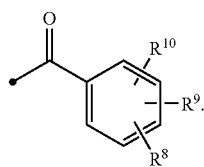

8. A compound according to claim 1, wherein:
ring A is phenyl;
$R^1$ is —$C(=NH)NH_2$, or $CH_2NH_2$;
$R^2$ is butyl, i-butyl, s-butyl, t-butyl, cyclopentyl, cyclopentyl-NHCO—$CH_2$—, cyclopentyl-$N(CH_3)CO$—$CH_2$—, cyclohexyl, cyclohexyl-NHCO—$CH_2$—, cyclohexyl-$N(CH_3)CO$—$CH_2$—, phenyl, phenyl-NHCO—, phenyl-NHCO—$CH_2$—, phenyl-$N(CH_3)CO$—$CH_2$—, 2-Me-phenyl-NHCO—$CH_2$—, 3-Me-phenyl-NHCO—$CH_2$—, 4-Me-phenyl-NHCO—$CH_2$—, 2-F-phenyl-NHCO—$CH_2$—, 3-F-phenyl-NHCO—$CH_2$—, 4-F-phenyl-NHCO—$CH_2$—, 2-OMe-phenyl-NHCO—$CH_2$—, 3-OMe-phenyl-NHCO—$CH_2$—, 4-OMe-phenyl-NHCO—$CH_2$—, benzyl, 3-$CO_2$H-benzyl, 4-$CO2$H-benzyl, benzyl-CO—, phenethyl, phenylpropyl, 2-pyridyl-NHCO—$CH_2$—, 3-pyridyl-NHCO—$CH_2$—, 4-pyridyl-NHCO—$CH_2$—, 2-thiazolyl-NHCO—$CH_2$—, 2-Me-2H-3-pyrazolyl-NHCO—$CH_2$—, $CO_2$H—$CH_2$—, $CO_2$H—$(CH_2)_2$—, —$CO_2$Me, —$SO_2$Me, —$CH_2CH_2OMe$, —$CH_2CH_2OPh$, —$CH_2CH_2NH_2$, —$CH_2CH_2NHCOMe$, —$CH_2CH_2NHCOPh$, —$CH_2CONH_2$, —$CH_2CONHMe$, —$CH_2CH_2NHCO_2Me$, —$CH_2CH_2NHCONHMe$, —$CH_2CH_2OH$, —$CH_2CH_2O(benzyl)$, —$CH_2CH_2NHSO_2Me$, —$CH_2CH_2CONHMe$, —$CH_2CH_2CONHPh$, 3-$CO_2$H-Ph, or 4-$CO_2$H-Ph; and
$R^8$, $R^9$, and $R^{10}$ are, independently at each occurrence, H, Me, Et, OMe, OH, Cl, $CF_3$, or $OCF_3$.

9. A compound according to claim 1, wherein the compound is selected from the group:
N-(2-benzylamino-4-carbamimidoyl-benzyl)-3,5-dimethoxy-4-methyl-benzamide;
N-(4-carbamimidoyl-2-isobutylamino-benzyl)-3,5-dimethoxy-4-methyl-benzamide;
N-(4-carbamimidoyl-2-phenylamino-benzyl)-3,5-dimethoxy-4-methyl-benzamide;
N-(4-carbamimidoyl-2-phenethylamino-benzyl)-3,5-dimethoxy-4-methyl-benzamide;
N-[4-carbamimidoyl-2-(3-phenyl-propylamino)-benzyl]-3,5-dimethoxy-4-methyl benzamide;
N-(4-carbamimidoyl-2-cyclopentylamino-benzyl)-3,5-dimethoxy-4-methyl-benzamide;
N-(4-carbamimidoyl-2-cyclohexylamino-benzyl)-3,5-dimethoxy-4-methyl-benzamide;
{5-carbamimidoyl-2-[(3,5-dimethoxy-4-methyl-benzoylamino)-methyl]-phenylamino}-acetic acid;
3-{5-carbamimidoyl-2-[(3,5-dimethoxy-4-methyl-benzoylamino)-methyl]-phenylamino}-propionic acid;
3-({5-carbamimidoyl-2-[(3,5-dimethoxy-4-methyl-benzoylamino)-methyl]-phenylamino}-methyl)-benzoic acid;
4-({5-carbamimidoyl-2-[(3,5-dimethoxy-4-methyl-benzoylamino)-methyl]-phenylamino}-methyl)-benzoic acid;
{5-carbamimidoyl-2-[(3,5-dimethoxy-4-methyl-benzoylamino)-methyl]-phenyl}-carbamic acid methyl ester;
N-[4-carbamimidoyl-2-(3-phenyl-ureido)-benzyl]-3,5-dimethoxy-4-methyl-benzamide;
N-(4-carbamimidoyl-2-methanesulfonylamino-benzyl)-3,5-dimethoxy-4-methyl-benzamide;
N-(4-carbamimidoyl-2-phenylacetylamino-benzyl)-3,5-dimethoxy-4-methyl-benzamide;
N-[4-carbamimidoyl-2-(phenethyl-phenylcarbamoylmethyl-amino)-benzyl]-3,5-dimethoxy-4-methyl-benzamide;
N-[4-carbamimidoyl-2-(phenylcarbamoylmethyl-amino)-benzyl]-3,5-dimethoxy-4-methyl-benzamide;
N-(4-carbamimidoyl-2-{methyl-[(methyl-phenyl-carbamoyl)-methyl]-amino}benzyl)-3,5-dimethoxy-4-methyl-benzamide;
N-{4-carbamimidoyl-2-[methyl-(pyridin-2-ylcarbamoylmethyl)-amino]-benzyl}-3,5-dimethoxy-4-methyl-benzamide;
N-{4-carbamimidoyl-2-[methyl-(pyridin-3-ylcarbamoylmethyl)-amino]-benzyl}-3,5-dimethoxy-4-methyl-benzamide;
N-{4-carbamimidoyl-2-[methyl-(pyrimidin-4-ylcarbamoylmethyl)-amino]-benzyl}-3,5-dimethoxy-4-methyl-benzamide;
N-{4-carbamimidoyl-2-[methyl-(o-tolylcarbamoyl-methyl)-amino]-benzyl}-3,5-dimethoxy-4-methyl-benzamide;
N-{4-carbamimidoyl-2-[methyl-(m-tolylcarbamoyl-methyl)-amino]-benzyl}-3,5-dimethoxy-4-methyl-benzamide;

N-{4-carbamimidoyl-2-[methyl-(p-tolylcarbamoyl-methyl)-amino]-benzyl}-3,5-dimethoxy-4-methyl-benzamide;
N-(4-carbamimidoyl-2-{[(2-fluoro-phenylcarbamoyl)-methyl]-methyl-amino}-benzyl)-3,5-dimethoxy-4-methyl-benzamide;
N-(4-carbamimidoyl-2-{[(3-fluoro-phenylcarbamoyl)-methyl]-methyl-amino}-benzyl)-3,5-dimethoxy-4-methyl-benzamide;
N-(4-carbamimidoyl-2-{[(4-fluoro-phenylcarbamoyl)-methyl]-methyl-amino}-benzyl)-3,5-dimethoxy-4-methyl-benzamide;
N-(4-carbamimidoyl-2-{[(2-methoxy-phenylcarbamoyl)-methyl]-methyl-amino}-benzyl)-3,5-dimethoxy4-methyl-benzamide;
N-(4-carbamimidoyl-2-{[(3-methoxy-phenylcarbamoyl)-methyl]-methyl-amino}-benzyl)-3,5-dimethoxy-4-methyl-benzamide;
N-(4-carbamimidoyl-2-{[(4-methoxy-phenylcarbamoyl)-methyl]-methyl-amino}-benzyl)-3,5-dimethoxy4-methyl-benzamide;
N-{4-carbamimidoyl-2-[methyl-(thiazol-2-ylcarbamoyl-methyl)-amino]-benzyl}-3,5-dimethoxy-4-methyl-benzamide;
N-(4-carbamimidoyl-2-{methyl-[(2-methyl-2H-pyrazol-3-ylcarbamoyl)-methyl]-amino}-benzyl)-3,5-dimethoxy-4-methyl-benzamide;
N-[$^4$-carbamimidoyl-2-(cyclohexylcarbamoylmethyl-methyl-amino)-benzyl]-3,5-dimethoxy4-methyl-benzamide;
N-[4-carbamimidoyl-2-(cyclopentylcarbamoylmethyl-methyl-amino)-benzyl]-3,5-dimethoxy-4-methyl-benzamide;
N-(4-carbamimidoyl-2-{[(cyclohexyl-methyl-carbamoyl)-methyl]-methyl-amino}-benzyl)-3,5-dimethoxy-4-methyl-benzamide;
N-(4-carbamimidoyl-2-(2-phenoxyethylamino)benzyl)-3,5-dimethoxy-4-methylbenzamide;
N-(4-carbamimidoyl-2-(2-methoxyethylamino)benzyl)-3,5-dimethoxy-4-methylbenzamide;
N-(2-(2-aminoethylamino)-4-carbamimidoylbenzyl)-3,5-dimethoxy-4-methylbenzamide;
N-(2-(2-acetamidoethylamino)-4-carbamimidoylbenzyl)-3,5-dimethoxy-4-methylbenzamide;
N-[2-(2-benzoylaminoethylamino)-4-carbamimidoylbenzyl]-3,5-dimethoxy-4-methylbenzamide;
N-(2-(2-amino-2-oxoethylamino)-4-carbamimidoylbenzyl)-3,5-dimethoxy-4-methylbenzamide;
N-(4-carbamimidoyl-2-(2-(methylamino)-2-oxoethylamino)benzyl)-3,5-dimethoxy-4-methylbenzamide;
methyl 2-(5-carbamimidoyl-2-((3,5-dimethoxy-4-methylbenzamido)methyl)phenylamino)ethylcarbamate;
1-(2-(5-carbamimidoyl-2-((3,5-dimethoxy-4-methylbenzamido)methyl)phenylamino)ethyl)-3-methylurea;
N-(4-carbamimidoyl-2-(2-hydroxyethylamino)benzyl)-3,5-dimethoxy-4-methylbenzamid;
N-(2-(2-(benzyloxy)ethylamino)-4-carbamimidoylbenzyl)-3,5-dimethoxy-4-methylbenzamide;
N-(4-carbamimidoyl-2-(2-(methylsulfonamido)ethylamino)benzyl)-3,5-dimethoxy-4-methylbenzamide;
N-(4-carbamimidoyl-2-(3-(methylamino)-3-oxopropylamino)benzyl)-3,5-dimethoxy-4-methylbenzamide;
N-(4-carbamimidoyl-2-(3-oxo-3-(phenylamino)propylamino)benzyl)-3,5-dimethoxy-4-methylbenzamide;
3-(5-carbamimidoyl-2-((3,5-dimethoxy-4-methylbenzamido)methyl)phenylamino)benzoic acid;
4-(5-carbamimidoyl-2-((3,5-dimethoxy-4-methylbenzamido)methyl)phenylamino)benzoic acid;
2-(5-carbamimidoyl-2-((3-(trifluoromethoxy)benzamido)methyl)phenylamino)acetic acid;
2-(5-carbamimidoyl-2-((3-ethylbenzamido)methyl)phenylamino)acetic acid;
2-(5-carbamimidoyl-2-((3-methylbenzamido)methyl)phenylamino)acetic acid;
2-(5-carbamimidoyl-2-((3,4-dimethylbenzamido)methyl)phenylamino)acetic acid;
2-(2-(benzamidomethyl)-5-carbamimidoylphenylamino)acetic acid;
2-(5-carbamimidoyl-2-((3-(trifluoromethyl)benzamido)methyl)phenylamino)acetic acid;
2-(5-carbamimidoyl-2-((3-chlorobenzamido)methyl)phenylamino)acetic acid;
2-(5-carbamimidoyl-2-((3-methoxybenzamido)methyl)phenylamino)acetic acid;
2-(5-carbamimidoyl-2-((3-hydroxybenzamido)methyl)phenylamino)acetic acid;
2-(5-carbamimidoyl-2-((3-methoxy-4-methylbenzamido)methyl)phenylamino)acetic acid; and
2-5-(aminomethyl)-2-((3,5-dimethoxy-4-methylbenzamido)methyl)phenylamino)acetic acid or a stereoisomer or pharmaceutically acceptable salt or solvate form thereof.

10. A pharmaceutical composition, comprising: a pharmaceutically acceptable carrier and a therapeutically effective amount of a compound of claim 1 or a pharmaceutically acceptable salt or solvate thereof.

11. A method for treating athromboembolic disorder selected from the group consisting of arterial cardiovascular thromboembolic disorders, venous cardiovascular thromboembolic disorders, and thromboembolic disorders in the chambers of the heart, comprising: administering to a patient in need thereof a therapeutically effective amount of a compound of claim 1 or a stereolsomer or a pharmaceutically acceptable salt or solvate thereof, wherein the method of treating is selected from inhibiting the disease-state or relieving the disease-state.

12. A method for treating a thromboembolic disorder selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis, comprising: administering to a patient in need thereof a therapeutically effective amount of a compound of claim 1 or a stereoisomer or a pharmaceutically acceptable salt or solvate thereof, wherein the method of treating is selected from inhibiting the disease-state or relieving the disease-state.

13. A pharmaceutical composition, comprising: a pharmaceutically acceptable carrier and a therapeutically effective amount of a compound of claim 2 or a pharmaceutically acceptable salt or solvate thereof.

14. A pharmaceutical composition, comprising: a pharmaceutically acceptable carrier and a therapeutically effective amount of a compound of claim 3 or a pharmaceutically acceptable salt or solvate thereof.

15. A pharmaceutical composition, comprising: a pharmaceutically acceptable carrier and a therapeutically effective amount of a compound of claim 4 or a pharmaceutically acceptable salt or solvate thereof.

16. A pharmaceutical composition, comprising: a pharmaceutically acceptable carrier and a therapeutically effective amount of a compound of claim 5 or a pharmaceutically acceptable salt or solvate thereof.

17. A pharmaceutical composition, comprising: a pharmaceutically acceptable carrier and a therapeutically effective amount of a compound of claim 6 or a pharmaceutically acceptable salt or solvate thereof.

18. A pharmaceutical composition, comprising: a pharmaceutically acceptable carrier and a therapeutically effective amount of a compound of claim 7 or a pharmaceutically acceptable salt or solvate thereof.

19. A pharmaceutical composition, comprising: a pharmaceutically acceptable carrier and a therapeutically effective amount of a compound of claim 8 or a pharmaceutically acceptable salt or solvate thereof.

20. A pharmaceutical composition, comprising: a pharmaceutically acceptable carrier and a therapeutically effective amount of a compound of claim 9 or a pharmaceutically acceptable salt or solvate thereof.

\* \* \* \* \*